(12) United States Patent
Saadat et al.

(10) Patent No.: US 12,257,001 B2
(45) Date of Patent: *Mar. 25, 2025

(54) DEVICES AND METHODS FOR TREATING A NERVE OF THE NASAL CAVITY USING IMAGE GUIDANCE

(71) Applicant: Arrinex, Inc., Redwood City, CA (US)

(72) Inventors: Vahid Saadat, Atherton, CA (US); William Jason Fox, San Mateo, CA (US); Mojgan Saadat, Atherton, CA (US)

(73) Assignee: Arrinex, Inc., Redwood City, CA (US)

( * ) Notice: Subject to any disclaimer, the term of this patent is extended or adjusted under 35 U.S.C. 154(b) by 1066 days.

This patent is subject to a terminal disclaimer.

(21) Appl. No.: 17/157,245

(22) Filed: Jan. 25, 2021

(65) Prior Publication Data

US 2021/0137610 A1    May 13, 2021

Related U.S. Application Data

(62) Division of application No. 15/655,832, filed on Jul. 20, 2017, now Pat. No. 10,939,965.

(Continued)

(51) Int. Cl.
*A61B 18/18* (2006.01)
*A61B 18/02* (2006.01)
(Continued)

(52) U.S. Cl.
CPC .............. *A61B 34/20* (2016.02); *A61B 18/02* (2013.01); *A61B 18/1492* (2013.01);
(Continued)

(58) Field of Classification Search
CPC . A61B 18/02; A61B 18/1485; A61B 18/1492; A61B 2018/00053;
(Continued)

(56) References Cited

U.S. PATENT DOCUMENTS

| 1,604,554 A | 5/1898 | Wise et al. |
| 5,971,979 A | 10/1999 | Joye et al. |

(Continued)

FOREIGN PATENT DOCUMENTS

| WO | 99020185 | 4/1999 |
| WO | 9927862 | 6/1999 |

(Continued)

OTHER PUBLICATIONS

Bicknell et al., "Cryosurgery for Allergic and Vasomotor Rhinitis", The Journal of Laryngology and Otology, vol. 93, Feb. 1979, 143-146.

(Continued)

*Primary Examiner* — Michael F Peffley
*Assistant Examiner* — Amanda L Zink
(74) *Attorney, Agent, or Firm* — McDonnell Boehnen Hulbert & Berghoff LLP

(57) ABSTRACT

The invention disclosed here generally relates to devices used to identify the location of a never in order to modify a property of the nerve. Specifically, the invention utilized pre-operative scans of a patient's nasal cavity in order to identify target treatment locations when a nerve to be treated is located. The image of the nasal cavity and target treatment location can be registered with the real time position of the nasal cavity using a surgical navigation system in order to assist in guiding a surgical probe to the target treatment location.

20 Claims, 17 Drawing Sheets

Related U.S. Application Data

(60) Provisional application No. 62/364,753, filed on Jul. 20, 2016.

(51) Int. Cl.
*A61B 18/14* (2006.01)
*A61B 34/20* (2016.01)
*A61B 18/00* (2006.01)

(52) U.S. Cl.
CPC ............ *A61B 2018/00214* (2013.01); *A61B 2018/00327* (2013.01); *A61B 2018/00434* (2013.01); *A61B 2018/00577* (2013.01); *A61B 2018/00982* (2013.01); *A61B 2018/0212* (2013.01); *A61B 2034/2051* (2016.02); *A61B 2034/2065* (2016.02); *A61B 2034/2072* (2016.02)

(58) Field of Classification Search
CPC .......... A61B 2018/00214; A61B 2018/00327; A61B 2018/00434; A61B 2018/00577; A61B 2018/00982; A61B 2018/0212; A61B 2034/2051; A61B 2034/2065; A61B 2034/2072; A61B 2090/374; A61B 2090/3762; A61B 34/20
See application file for complete search history.

(56) References Cited

U.S. PATENT DOCUMENTS

| | | | |
|---|---|---|---|
| 6,064,905 A * | 5/2000 | Webster, Jr. ......... | A61B 5/6852 600/509 |
| 6,283,959 B1 | 9/2001 | Lalonde et al. | |
| 6,355,029 B1 | 3/2002 | Joye et al. | |
| 6,375,654 B1 | 4/2002 | McIntyre | |
| 6,428,534 B1 | 8/2002 | Joye et al. | |
| 6,432,102 B2 | 8/2002 | Joye et al. | |
| 6,514,245 B1 | 2/2003 | Williams et al. | |
| 6,517,533 B1 | 2/2003 | Swaminathan | |
| 6,537,271 B1 | 3/2003 | Murray et al. | |
| 6,575,966 B2 | 6/2003 | Lane et al. | |
| 6,595,988 B2 | 7/2003 | Wittenberger et al. | |
| 6,602,276 B2 | 8/2003 | Dobak, III et al. | |
| 6,648,879 B2 | 11/2003 | Joye et al. | |
| 6,666,858 B2 | 12/2003 | Lafontaine | |
| 6,673,066 B2 | 1/2004 | Werneth | |
| 6,685,732 B2 | 2/2004 | Kramer | |
| 6,736,809 B2 | 5/2004 | Capuano et al. | |
| 6,786,900 B2 | 9/2004 | Joye et al. | |
| 6,786,901 B2 | 9/2004 | Joye et al. | |
| 6,811,550 B2 | 11/2004 | Holland et al. | |
| 6,875,209 B2 | 4/2005 | Zvuloni et al. | |
| 6,905,494 B2 | 6/2005 | Yon et al. | |
| 6,908,462 B2 | 6/2005 | Joye et al. | |
| 6,949,096 B2 | 9/2005 | Davison et al. | |
| 6,972,015 B2 | 12/2005 | Joye et al. | |
| 6,989,009 B2 | 1/2006 | Lafontaine | |
| 6,991,631 B2 | 1/2006 | Woloszko et al. | |
| 7,001,378 B2 | 2/2006 | Yon et al. | |
| 7,060,062 B2 | 6/2006 | Joye et al. | |
| 7,081,112 B2 | 7/2006 | Joye et al. | |
| 7,101,368 B2 | 9/2006 | Lafontaine | |
| 7,189,227 B2 | 3/2007 | Lafontaine | |
| 7,288,089 B2 | 10/2007 | Yon et al. | |
| 7,291,144 B2 | 11/2007 | Dobak, III et al. | |
| 7,300,433 B2 | 11/2007 | Lane et al. | |
| 7,354,434 B2 | 4/2008 | Zvuloni et al. | |
| 7,442,190 B2 | 10/2008 | Abboud et al. | |
| 7,449,018 B2 | 11/2008 | Kramer | |
| 7,527,622 B2 | 5/2009 | Lane et al. | |
| 7,641,679 B2 | 1/2010 | Joye et al. | |
| 7,648,497 B2 | 1/2010 | Lane et al. | |
| 7,720,521 B2 * | 5/2010 | Chang ............... | A61M 25/10 600/199 |
| 7,727,191 B2 | 6/2010 | Mihalik et al. | |
| 7,727,228 B2 | 6/2010 | Abboud et al. | |
| 7,740,627 B2 | 6/2010 | Gammie et al. | |
| 7,771,409 B2 * | 8/2010 | Chang ................... | A61M 25/09 604/514 |
| 7,794,455 B2 | 9/2010 | Abboud et al. | |
| 7,842,031 B2 | 11/2010 | Abboud et al. | |
| 7,862,557 B2 | 1/2011 | Joye et al. | |
| 7,892,230 B2 | 2/2011 | Woloszko | |
| 8,043,283 B2 | 10/2011 | Dobak, III et al. | |
| 8,043,351 B2 | 10/2011 | Yon et al. | |
| 8,157,794 B2 | 4/2012 | Dobak, III et al. | |
| 8,172,828 B2 * | 5/2012 | Chang ................. | A61F 2/186 604/509 |
| 8,177,779 B2 | 5/2012 | Joye et al. | |
| 8,187,261 B2 | 5/2012 | Watson | |
| 8,235,976 B2 | 8/2012 | Lafontaine | |
| 8,292,887 B2 | 10/2012 | Woloszko et al. | |
| 8,298,217 B2 | 10/2012 | Lane et al. | |
| 8,333,758 B2 | 12/2012 | Joye et al. | |
| 8,382,747 B2 | 2/2013 | Abboud et al. | |
| 8,425,456 B2 | 4/2013 | Wihalik et al. | |
| 8,439,906 B2 | 5/2013 | Watson | |
| 8,465,481 B2 | 6/2013 | Mazzone et al. | |
| 8,475,440 B2 | 7/2013 | Abboud et al. | |
| 8,480,664 B2 | 7/2013 | Watson et al. | |
| 8,491,636 B2 | 7/2013 | Abboud et al. | |
| 8,512,324 B2 | 8/2013 | Abboud et al. | |
| 8,545,491 B2 | 10/2013 | Abboud et al. | |
| 8,591,504 B2 | 11/2013 | Tin | |
| 8,617,149 B2 | 12/2013 | Lafontaine et al. | |
| 8,632,529 B2 | 1/2014 | Bencini | |
| 8,663,211 B2 | 3/2014 | Fourkas et al. | |
| 8,672,930 B2 | 3/2014 | Wittenberger | |
| 8,679,104 B2 | 3/2014 | Abboud et al. | |
| 8,679,105 B2 | 3/2014 | Wittenberger et al. | |
| 8,715,274 B2 | 5/2014 | Watson | |
| 8,747,401 B2 | 6/2014 | Gonzalez et al. | |
| 8,764,740 B2 | 7/2014 | Watson | |
| 8,771,264 B2 | 7/2014 | Abboud et al. | |
| 8,827,952 B2 | 9/2014 | Subramaniam et al. | |
| 8,900,222 B2 | 12/2014 | Abboud et al. | |
| 8,911,434 B2 | 12/2014 | Wittenberger | |
| 8,926,602 B2 | 1/2015 | Pageard | |
| 8,936,594 B2 | 1/2015 | Wolf | |
| 8,945,107 B2 | 2/2015 | Buckley et al. | |
| 8,986,293 B2 | 3/2015 | Desrochers | |
| 8,986,301 B2 | 3/2015 | Wolf et al. | |
| 9,050,074 B2 | 6/2015 | Joye et al. | |
| 9,060,754 B2 | 6/2015 | Buckley et al. | |
| 9,060,755 B2 | 6/2015 | Buckley et al. | |
| 9,066,713 B2 | 6/2015 | Turovskiy | |
| 9,072,597 B2 | 7/2015 | Wolf et al. | |
| 9,084,590 B2 | 7/2015 | Wittenberger et al. | |
| 9,084,592 B2 | 7/2015 | Wu et al. | |
| 9,089,314 B2 | 7/2015 | Wittenberger | |
| 9,168,079 B2 | 10/2015 | Lalonde | |
| 9,179,964 B2 | 11/2015 | Wolf et al. | |
| 9,179,967 B2 | 11/2015 | Wolf et al. | |
| 9,211,393 B2 | 12/2015 | Hu et al. | |
| 9,220,556 B2 | 12/2015 | Lalonde et al. | |
| 9,237,924 B2 | 1/2016 | Wolf et al. | |
| 9,241,752 B2 | 1/2016 | Nash et al. | |
| 9,254,166 B2 | 2/2016 | Aluru et al. | |
| 9,333,023 B2 | 5/2016 | Wittenaberger | |
| 9,414,878 B1 | 8/2016 | Wu et al. | |
| 9,415,194 B2 | 8/2016 | Wolf et al. | |
| 9,433,463 B2 | 9/2016 | Wolf et al. | |
| 9,439,709 B2 | 9/2016 | Duong et al. | |
| 9,445,859 B2 | 9/2016 | Pageard | |
| 9,452,010 B2 | 9/2016 | Wolf et al. | |
| 9,480,521 B2 | 11/2016 | Kim et al. | |
| 9,486,278 B2 | 11/2016 | Wolf et al. | |
| 9,522,030 B2 | 12/2016 | Harmouche et al. | |
| 9,526,571 B2 | 12/2016 | Wolf et al. | |
| 9,555,223 B2 | 1/2017 | Abboud et al. | |
| 9,572,536 B2 | 2/2017 | Abboud et al. | |
| 9,763,743 B2 * | 9/2017 | Lin ................. | A61B 90/30 |
| 9,801,752 B2 | 10/2017 | Scott et al. | |

(56) References Cited

U.S. PATENT DOCUMENTS

| | | | |
|---|---|---|---|
| 10,092,355 B1* | 10/2018 | Hannaford | A61B 90/39 |
| 2003/0144659 A1 | 7/2003 | Edwards et al. | |
| 2008/0009851 A1 | 1/2008 | Wittenberger et al. | |
| 2008/0009925 A1 | 1/2008 | Abboud et al. | |
| 2008/0027423 A1 | 1/2008 | Choi et al. | |
| 2009/0182318 A1 | 7/2009 | Abboud et al. | |
| 2009/0234345 A1 | 9/2009 | Hon | |
| 2012/0029493 A1 | 2/2012 | Wittenberger et al. | |
| 2013/0218151 A1 | 8/2013 | Mihalik et al. | |
| 2014/0058369 A1 | 2/2014 | Hon | |
| 2014/0207130 A1 | 7/2014 | Fourkas et al. | |
| 2015/0045781 A1 | 2/2015 | Abboud et al. | |
| 2015/0119868 A1 | 4/2015 | Lalonde et al. | |
| 2015/0157382 A1 | 6/2015 | Avitall et al. | |
| 2015/0164571 A1 | 6/2015 | Saadat | |
| 2015/0190188 A1 | 7/2015 | Lalonde et al. | |
| 2015/0196740 A1 | 7/2015 | Mallin et al. | |
| 2015/0223860 A1 | 8/2015 | Wittenberger et al. | |
| 2015/0250524 A1 | 9/2015 | Moriarty et al. | |
| 2015/0265329 A1 | 9/2015 | Lalonde et al. | |
| 2015/0265812 A1 | 9/2015 | Lalonde | |
| 2016/0038212 A1 | 2/2016 | Ryba et al. | |
| 2016/0045277 A1 | 2/2016 | Lin et al. | |
| 2016/0066975 A1 | 3/2016 | Fourkas et al. | |
| 2016/0074090 A1 | 3/2016 | Lalonde et al. | |
| 2016/0143683 A1 | 5/2016 | Aluru et al. | |
| 2016/0166305 A1 | 6/2016 | Nash et al. | |
| 2016/0166306 A1 | 6/2016 | Pageard | |
| 2016/0220295 A1 | 8/2016 | Wittenberger | |
| 2016/0287315 A1 | 10/2016 | Wolf et al. | |
| 2016/0331433 A1 | 11/2016 | Wu et al. | |
| 2016/0331459 A1 | 11/2016 | Townley et al. | |
| 2016/0354134 A1 | 12/2016 | Pageard | |
| 2016/0354135 A1 | 12/2016 | Saadat | |
| 2016/0354136 A1 | 12/2016 | Saadat | |
| 2016/0361112 A1 | 12/2016 | Wolf et al. | |
| 2017/0007316 A1 | 1/2017 | Wolf et al. | |
| 2017/0014258 A1 | 1/2017 | Wolf et al. | |
| 2017/0042601 A1 | 2/2017 | Kim et al. | |
| 2017/0056087 A1 | 3/2017 | Buckley et al. | |
| 2017/0056632 A1 | 3/2017 | Jenkins et al. | |

FOREIGN PATENT DOCUMENTS

| | | |
|---|---|---|
| WO | 99030655 | 6/1999 |
| WO | 0009053 | 2/2000 |
| WO | 0047118 | 8/2000 |
| WO | 0054684 | 9/2000 |
| WO | 0164145 | 9/2001 |
| WO | 01095819 | 12/2001 |
| WO | 0204042 | 1/2002 |
| WO | 0207628 | 4/2002 |
| WO | 02069862 | 9/2002 |
| WO | 0200128 | 11/2002 |
| WO | 02083196 | 2/2003 |
| WO | 03013653 | 2/2003 |
| WO | 03026719 | 4/2003 |
| WO | 03051214 | 6/2003 |
| WO | 03028524 | 10/2003 |
| WO | 03020334 | 12/2003 |
| WO | 03088857 | 12/2003 |
| WO | 2004000092 | 12/2003 |
| WO | 2005089853 | 11/2005 |
| WO | 2004108207 | 12/2005 |
| WO | 2006002337 | 1/2006 |
| WO | 2006118725 | 11/2006 |
| WO | 2006119615 | 11/2006 |
| WO | 2006124176 | 11/2006 |
| WO | 2006017073 | 4/2007 |
| WO | 2007145759 | 12/2007 |
| WO | 2008000065 | 1/2008 |
| WO | 2008042890 | 4/2008 |
| WO | 2008046183 | 4/2008 |
| WO | 2008157042 | 12/2008 |
| WO | 2009114701 | 9/2009 |
| WO | 2009146372 | 12/2009 |
| WO | 2010081221 | 7/2010 |
| WO | 2010083281 | 7/2010 |
| WO | 2010111122 | 9/2010 |
| WO | 2011014812 | 2/2011 |
| WO | 2011091507 | 8/2011 |
| WO | 2011091508 | 8/2011 |
| WO | 2011091509 | 8/2011 |
| WO | 2011091533 | 8/2011 |
| WO | 2012012868 | 2/2012 |
| WO | 2012012869 | 2/2012 |
| WO | 2012015636 | 2/2012 |
| WO | 2012019156 | 2/2012 |
| WO | 2012051697 | 4/2012 |
| WO | 2012027641 | 5/2012 |
| WO | 2012058156 | 5/2012 |
| WO | 2012058159 | 5/2012 |
| WO | 2012058160 | 5/2012 |
| WO | 2012058161 | 5/2012 |
| WO | 2012058165 | 5/2012 |
| WO | 2012058167 | 5/2012 |
| WO | 2012174161 | 12/2012 |
| WO | 2013110156 | 8/2013 |
| WO | 2013163325 | 2/2014 |
| WO | 2014113864 | 7/2014 |
| WO | 2014138866 | 9/2014 |
| WO | 2014138867 | 9/2014 |
| WO | 2015038523 | 3/2015 |
| WO | 2015048806 | 4/2015 |
| WO | 2015061883 | 5/2015 |
| WO | 2015081420 | 6/2015 |
| WO | 2015106335 | 7/2015 |
| WO | 2015114038 | 8/2015 |
| WO | 2015139117 | 9/2015 |
| WO | 2015139118 | 9/2015 |
| WO | 2015153696 | 10/2015 |
| WO | 2016183337 | 11/2016 |
| WO | 2016186964 | 11/2016 |
| WO | 2017034705 | 3/2017 |
| WO | 2017047543 | 3/2017 |
| WO | 2017047545 | 3/2017 |

OTHER PUBLICATIONS

Bluestone et al., "Instranasal Freezing for Severe Epistaxis", Arch Otolaryngol. 85, Apr. 1967, 199-121.

Bumsted, "Cryotherapy for Chronic Vasomotor Rhinitis: Technique and Patient Selection for Improved Results", Laryngoscope, vol. 94, Apr. 1984, pp. 539-544.

Costa et al., "radiographic and Anatomic Characterization of the Nasal Septal Swell Body", Arch Otolaryngol Head Neck Surg., vol. 136, No. 11, Nov. 2010, 1109.

Girdhar-Gopal, "An Assessment of Postganglionic CryoneurolysIs for Managing Vasomotor Rhinitis", American Journal of Rhinology, vol. 8, No. 4 Jul.-Aug. 1994, pp. 157-164.

Golhar et al., "The Effect of Cryodestruction of Vidian Nasal Branches on Nasal Mucus Flow in Vasomotor Rhinitis", Indian Journal of of Otolaryngology, vol. 33, No. 1, Mar. 1981, pp. 12-14.

Hadoura et al., Mapping Surgical Coordinates of the Sphenopalatine Foramen: Surgical Navigation Study, The Journal of Laryngology and Otology, 123, pp. 742-745.

Ozenberger, "Cryosurgery in Chronic Rhinitis", The Laryngoscope, vol. 80, No. 5, May 1970, pp. 723-734.

Principato, "Chronic Vaomotor Rhinitis: Cryogenic and Other Surgical Modes of Treatment", The Laryngoscope, vol. 89, 1979, pp. 619-638.

Sanu, "Two Hundred Years of Controversy Between UK and USA", Rhinology, 86-91.

Settipane et al., "Update on Non allergic Rhinitis", Annals of Allergy Asthma & Immunology, vol. 86, 2001 494-508.

Terao et al., "Cryosurgery on Postganglionic Fibers (Posterior Nasal Branches) Of The Pterygopalatine Ganglion for Vasomotor Rhinitis", Acta Otolaryngol., vol. 96, 1983, pp. 139-148.

* cited by examiner

DEVICES AND METHODS FOR TREATING A NERVE OF THE NASAL CAVITY USING IMAGE GUIDANCE

CROSS-REFERENCES TO RELATED APPLICATIONS

The present application is a divisional of U.S. patent application Ser. No. 15/655,832, filed Jul. 20, 2017 (issued as U.S. Pat. No. 10,939,965 on Mar. 9, 2021), which claims the benefit of U.S. Provisional Patent Application No. 62/364,753 filed Jul. 20, 2016, entitled "Image Guided Surgical Procedures", the contents of which are incorporated herein by reference in their entirety for all purposes.

BACKGROUND OF THE INVENTION

The nose includes the external nose on the face and the nasal cavity, which extends posteriorly from it. The nose functions in smell and provides filtered, warm, moist air for inspiration. The external nose presents a root (or bridge), a dorsum, and a free tip or apex. The two inferior openings are the nostrils (or nares), bounded laterally by the ala and medially by the nasal septum. The superior part of the nose is supported by the nasal, frontal, and maxillary bones; the inferior part includes several cartilages. The continuous free margin of the nasal bones and maxillae in a dried skull is termed the piriform aperture. The nasal cavity extends in an antero-posterior direction from the nostrils to the choanae. The choanae are the posterior apertures of the nose. Each choana is bounded medially by the vomer, inferiorly by the horizontal plate of the palatine bone, laterally by the medial pterygoid plate, and superiorly by the body of the sphenoid bone. Posteriorly, the nasal cavity communicates with the nasopharynx, which in many respects may be regarded as the posterior portion of the cavity. The nasal cavity is related to the anterior and middle cranial fossae, orbit, and paranasal sinuses and is separated from the oral cavity by the hard palate. In addition to the nostrils and choanae, the nasal cavity presents openings for the paranasal sinuses and the nasolacrimal duct. Further openings, covered by mucosa in vivo, are found in a dried skull, e.g., the sphenopalatine foramen. The nasal cavity is divided into right and left halves, each of which may be termed a nasal cavity, by the nasal septum. Each half has a roof, floor, and medial and lateral walls. The roof of the nasal cavity is formed by nasal cartilages and several bones, chiefly the nasal and frontal bones, the cribriform plate of the ethmoid, and the body of the sphenoid. The floor, wider than the roof, is formed by the palatine process of the maxilla and the horizontal plate of the palatine bone, i.e., by the palate. The medial wall, or nasal septum, is formed (from anterior to posterior) by the septal cartilage, the perpendicular plate of the ethmoid bone, and the vomer. The lateral wall is uneven and complicated and is formed by several bones: nasal, maxilla, lacrimal and ethmoid, inferior nasal turbinate, perpendicular plate of palatine, and medial pterygoid plate of sphenoid The lateral wall presents three medial projections termed nasal turbinates, which overlie passages (meatuses). The inferior turbinate is a separate bone; the others are portions of the ethmoid bone. The superior meatus, under cover of the superior turbinate, receives the openings of the posterior ethmoidal cells and (in a dried skull) the sphenopalatine foramen. The middle meatus, under cover of the middle turbinate, receives the openings of the maxillary and frontal sinuses. Most anterior ethmoidal cells open on an elevation (ethmoidal bulla). A curved slit (hiatus semilunaris) inferior to the bulla receives the opening of the maxillary sinus. The frontal sinus and some anterior ethmoidal cells open either into an extension (ethmoidal infundibulum) of the hiatus or directly into the anterior part (frontal recess) of the middle meatus. The inferior meatus, which lies between the inferior turbinate and the palate, receives the termination of the nasolacrimal duct. The nasal cavity is continuously covered by mucosa. The posterior two thirds have active ciliary motion for rapid drainage backward and downward into the nasopharynx. The nasal mucosa is highly vascular, and it warms and moistens the incoming air. The mucosa contains large venous-like spaces ("swell bodies"), which may become congested during allergic reactions or infections. The mucosa's functionality is controlled by the nerves that innervate the nasal cavity. The nerves are responsible for sensations of touch, pressure, temperature, and regulation of blood supply and secretion of the nasal mucosa. These nerves include the anterior ethmoid nerve (AEN), the nasopalatine nerve (NPN), the posterior inferior branch of the greater palatine nerve (GPN), and the posterior nasal nerve (PNN). Figure below shows a map of the innervation.

The anterior ethmoid nerve is the continuation of the nasociliary nerve. It innervates the nasal cavity at the anterior ethmoidal foramen and the nasal slit. This nerve supply sensory fibers to the mucosa of the ethmoidal sinuses, the anterior aspect of the nasal cavity, and the skin on the lateral sides of the nose. The nasopalatine nerve is a branch from the sphenopalatine ganglion (SPG), it innervates the nasal cavity through the sphenopalatine foramen (SPF), once in the nasal cavity it passes along the roof of the nose and into the nasal septum and courses its way down the nasal septum, and through the incisive foramen to supply the mucous membrane of the hard palate. At the ganglion, it receives parasympathetic fibers which supply the nasal and palatine mucosal glands as well as special sensory fibers (taste). The posterior inferior branch of the greater palatine nerve branches off the greater palatine nerve in the greater palatine canal and exits the canal through a tiny un-named foramen in the palatine bone to enter the nasal cavity. In the lateral wall of the nasal cavity it supplies the posterior inferior mucosa including the inferior concha and middle and inferior meatus. At the sphenopalatine ganglion, it also receives parasympathetic fibers which are carried by the greater palatine nerve before it branches off that supply nasal glands. The posterior nasal nerve also branches from the ganglion and enters the nasal cavity through the SPF. At the ganglion, it receives parasympathetic fibers which supply nasal glands. It leaves the fossa inferomedially through the sphenopalatine foramen with the nasopalatine nerve to enter the posterosuperior nasal cavity just behind the superior nasal meatus where it divides into the medial and lateral branch. Medial branches supply the posterosuperior quadrant of the nasal septum and the lateral branches supply the posterosuperior quadrant of the lateral nasal wall.

FIGS. 1A-1E illustrate various views of the nasal cavity including showing the anatomical features noted above.

Disorders involving these nerves have been linked to rhinitis symptoms including runny nose, nasal congestion, sneezing, and itching, as well as, chronic pain, cluster headaches, and migraines. Various treatments including physically damaging (comprising, cutting, or removing), thermal ablating, or chemically altering of these nerves have shown to provide relief to patients that suffer from the above ailments. An example of therapies targeting nasal nerves to address these ailments are described in U.S. patent application Ser. No. 15/242,362 filed Aug. 19, 2016, entitled "APPARATUS AND METHODS FOR TREATING RHINITIS", which is incorporated herein by reference in its entirety for all purposes.

A challenge in treating the symptoms of rhinitis is accurately targeting the desired nerve as well as the branches of the nerve as the nerve fibers branch throughout the nasal mucosa and are not visible on the surface of the mucosa, for example using an endoscope. One method physicians use in an attempts to identify the nerves is by making an incision in the mucosa, and pulling the mucosa away from the bone. This method has the disadvantage of requiring general anesthesia and further the procedure is invasive and requires a lengthy recovery time. Another method physicians use to attempt to identify the nerves is by identifying visible landmarks using a rigid endoscope and define the treatment area to treat around the areas where the nerve fibers are predicted to be based on the visible landmarks. This approach has the disadvantages of being imprecise. In some cases, this method proves to be challenging because a large percentage of the patients having the procedure performed previously have underwent other procedures that have altered these surface visual anatomical landmarks that are used to identify innervation and/or these patient's mucosa is inflamed making it challenging to advance an endoscope into the nasal cavity to visualize landmarks when present.

Therefore there exists a need for identifying the location of nerves within the nasal cavity that is not invasive and is precise even in the patients with altered surface visual landmarks or inflamed mucosa.

BRIEF SUMMARY OF THE INVENTION

The present technology utilizes image-guided surgery (IGS) to assist a physician with identifying nerves to be targeted in the treatment of rhinitis and other conditions.

Embodiments of the present technology address the need for identifying the location of nerves noted above by providing a nerve treatment instrument with one or more location sensors that are trackable with a surgical navigation system. Target treatment areas may be identified pre-operatively using scan of the nasal cavity that are used by the surgical navigation system during the procedure to assist the physician with navigating a surgical probe using real-time 3-D imaging feedback of location to multiple anatomical landmarks. With the technology disclosed herein, physicians are able to pinpoint anatomical landmarks and location of their instruments in the nasal cavity with minimal direct visualization and are able to identify landmarks even if the surface has been altered by a previous surgery. This enables the physicians to more confidentially identify potential locations of the nerves to be treated without cutting the mucosa.

Further aspects, details and embodiments of the present invention will be understood by those of skill in the art upon reading the following detailed description of the invention and the accompanying drawings.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1A:
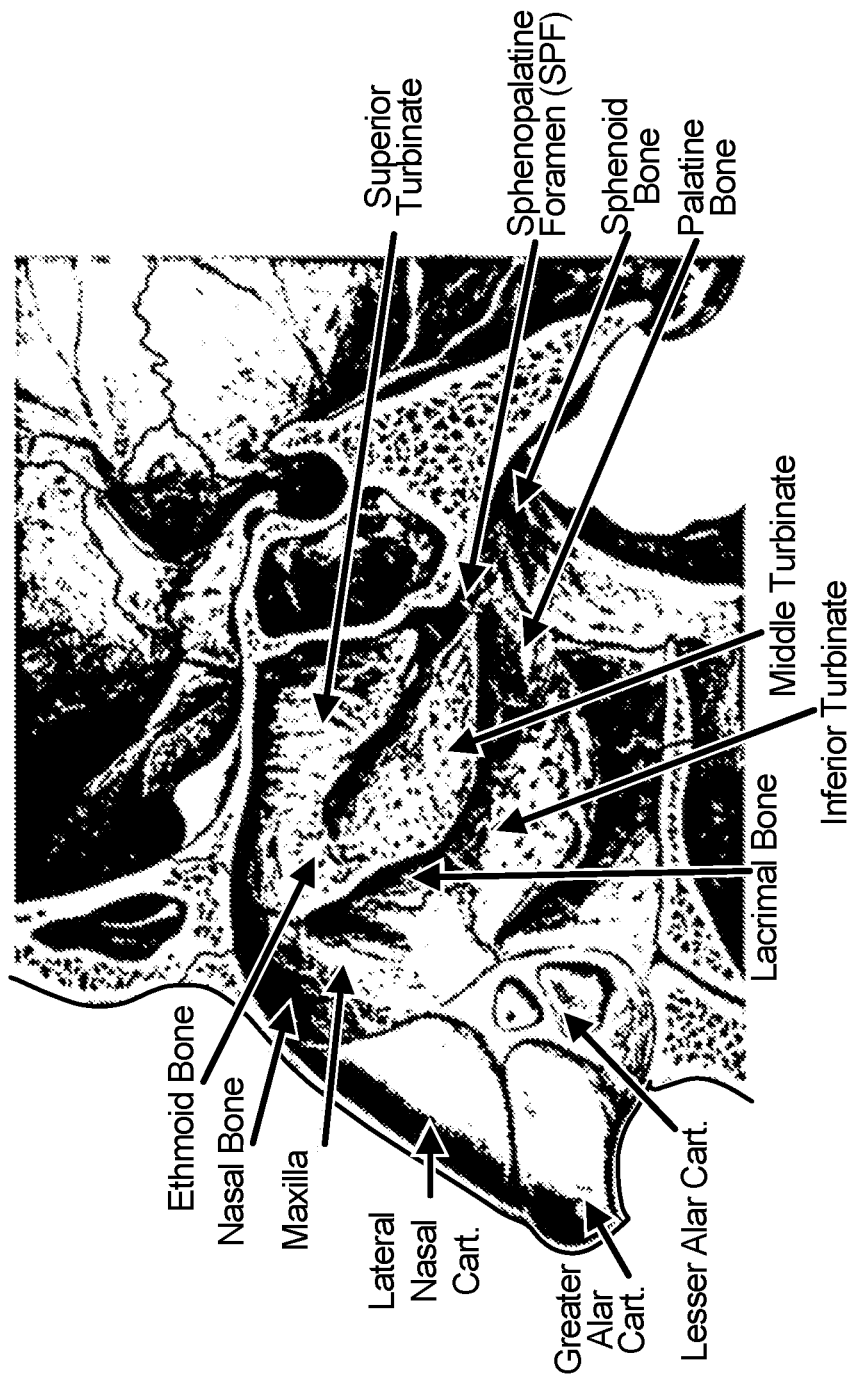
FIGS. 1A-1E shows various view of nasal cavity anatomy.
Figure 1B:
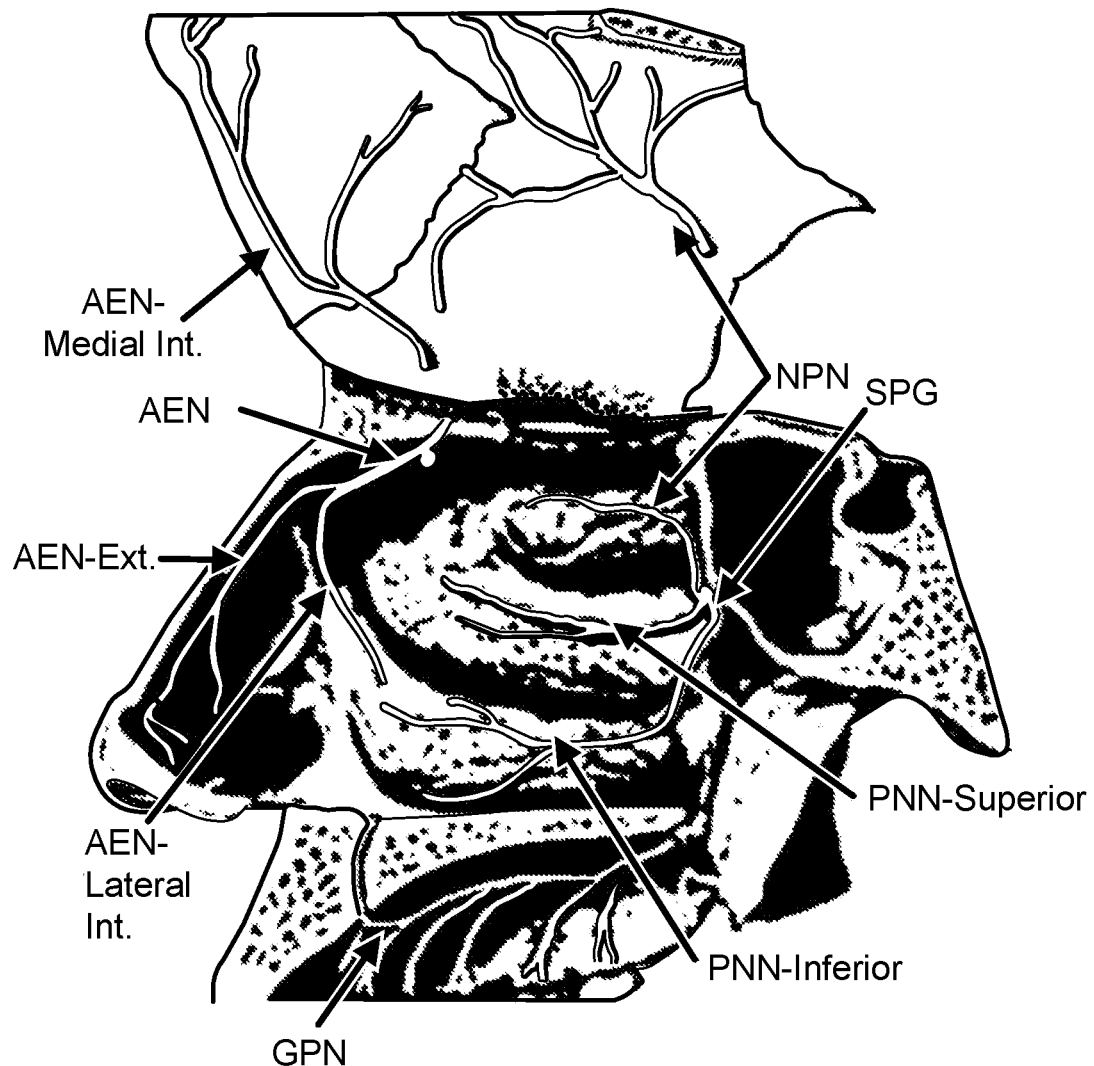
Figure 1C:
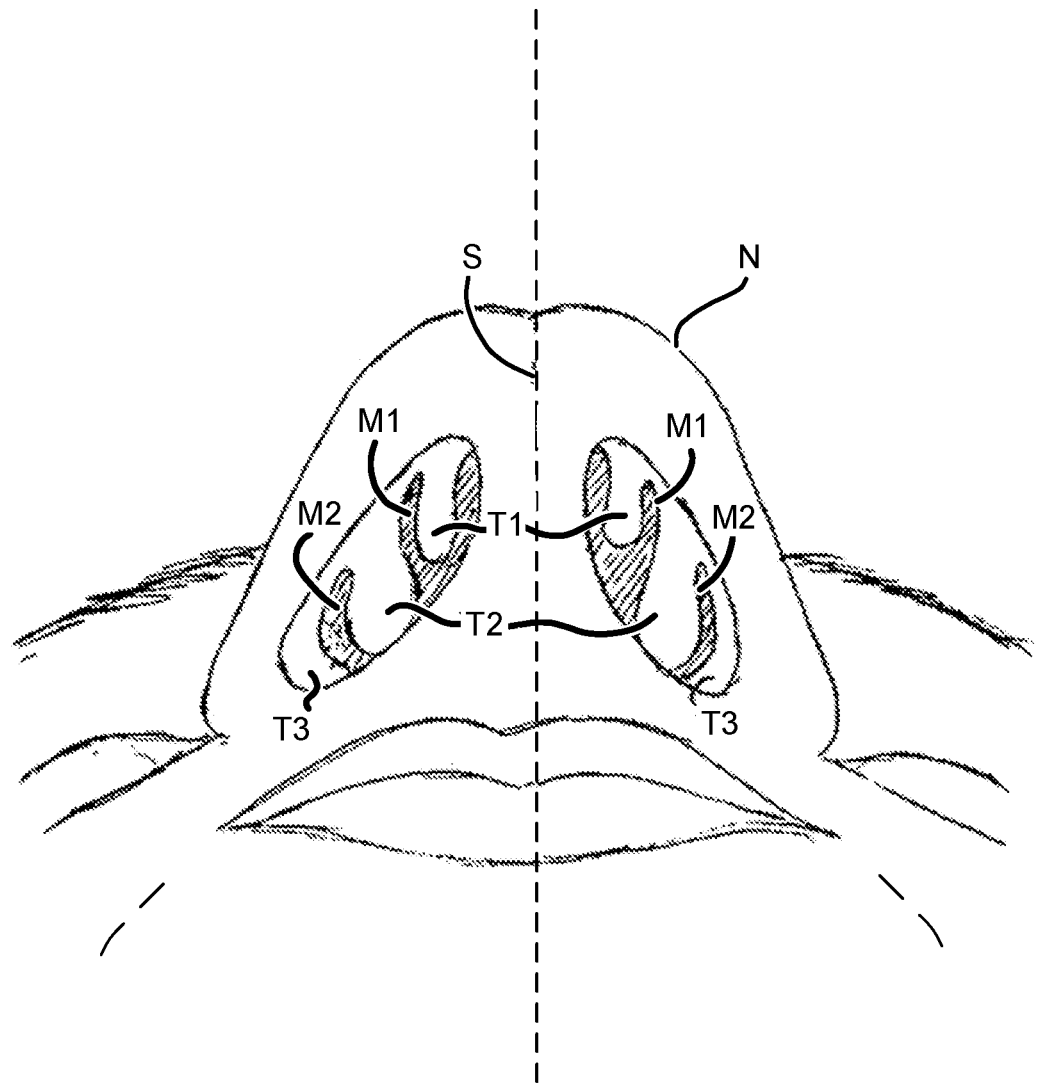
Figure 1D:
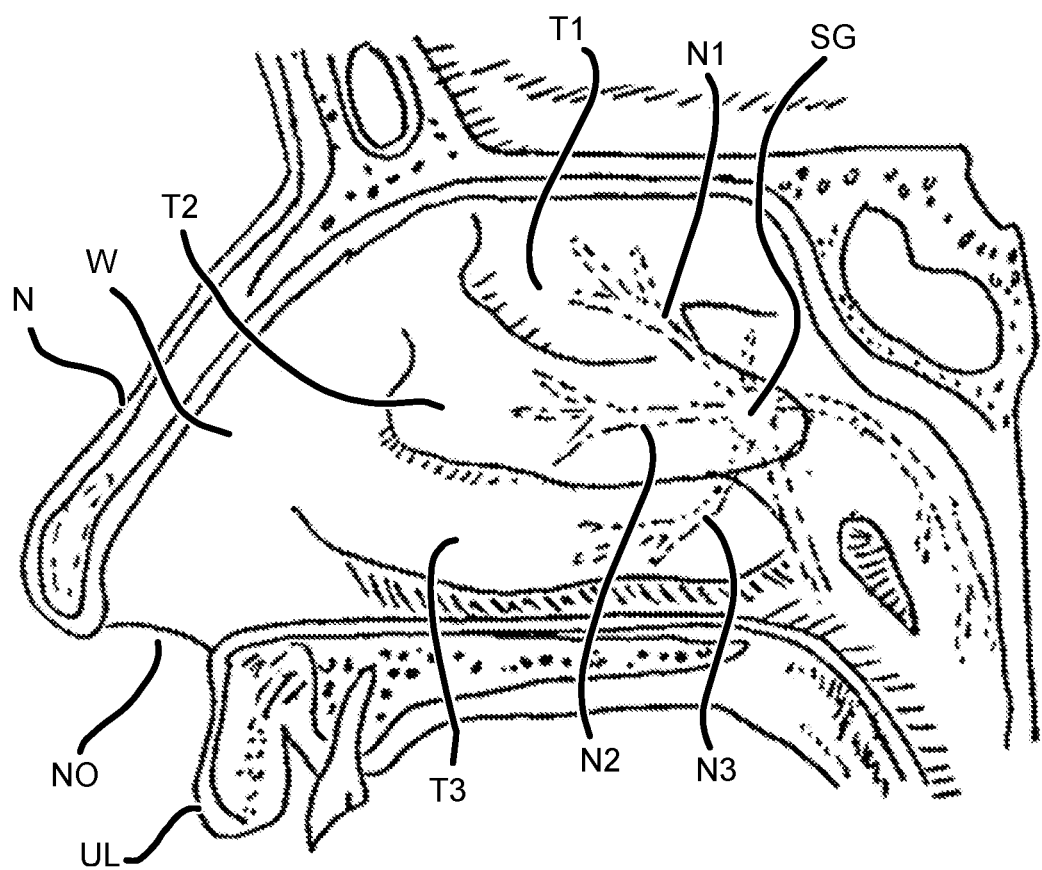
Figure 1E:
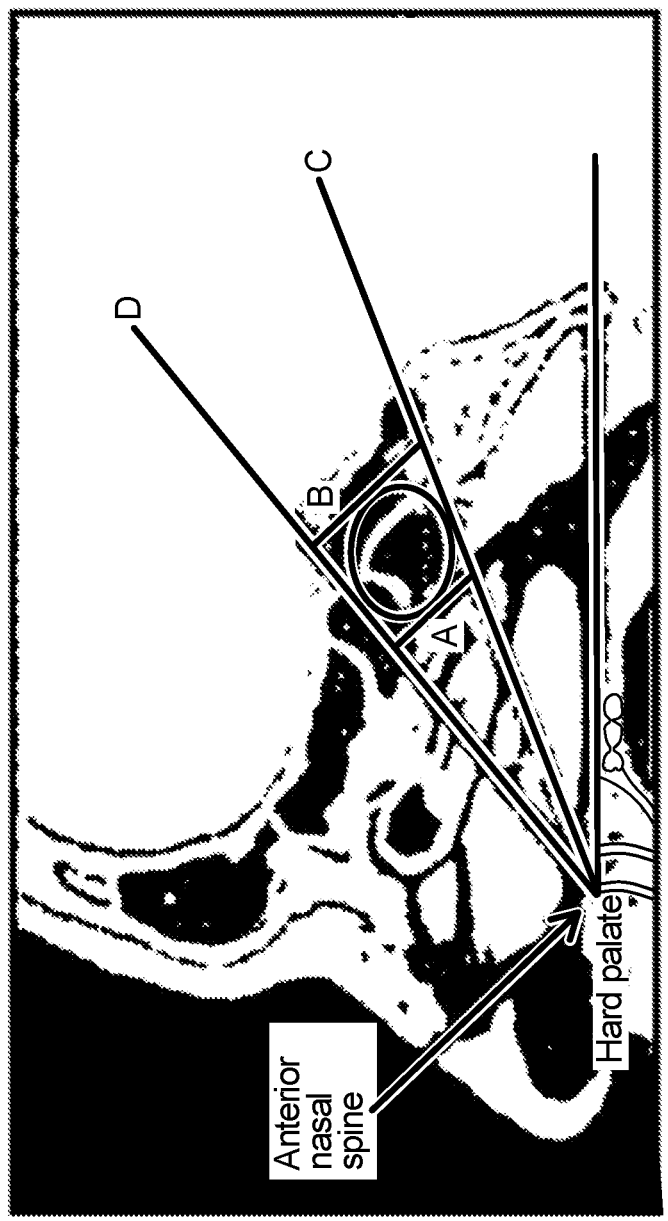

The present invention generally relates to medical devices, systems and methods, and more particularly relates to devices, systems and methods that treat rhinitis. Such treatment of rhinitis is achieved by decreasing or interrupting nerve signals that are transmitted from the sphenopalatine ganglion to the nasal mucosa via the posterior nasal nerves. A decrease or interruption of nerve signals can be attained by a variety of methods, particularly by the application of physical therapies (compression or cutting), thermal therapies (heat or cold), or chemical therapies (alcohol or anesthetic injections). Examples of thermal therapies include cryotherapy, cryoneuromodulation, cryomodulation, cryolysis, cryoablation, and thermoablation. It has been found that a specific target area within the nasal cavity is particularly effective in treating rhinitis.

The present technology may include a surgical navigation device which is used for Image guided surgery (IGS) procedures. The surgical navigation device may include a computer work station, a video monitor, a localizer and a sensor tracking system. The sensor tracking system is configured to track the location of one or more location sensors that be may be attached to surgical instruments. The location sensors mounted on the surgical instruments and the corresponding tracking system may be optical, electromagnetic or electromechanical.

Prior to an ablation procedure being performed, a patient may have a digital tomographic scan performed of their nasal cavity. The digital tomographic scan may be converted into a digital map which can be viewed on a computer with one or more two-dimensional views, and/or a three-dimensional view of the nasal cavity. The digital map may also be referred to as an image of the nasal cavity. As will be discussed below, the image of the nasal cavity may be used to identify target treatment locations within the nasal cavity.

In order to utilize the pre-operative image of the nasal cavity during an ablation procedure the image is registered to the position of the patient and the surgical tools in a common reference frame. In embodiments, a localizer is used to register the preoperative tomographic image data with the real time physical position of the patient's body, particularly the patient's nasal cavity, during the ablation procedures described herein. The sensor tracking system serves to track the position of each location sensor-equipped surgical instrument during the surgery and to communicate such information to the computer workstation. Registration is the process of matching two sets of data and in this case matching the image of the nasal cavity from the preoperative tomographic scan to intraoperative patient body position data so that the image displayed on the monitor of the surgical navigation device will show the positions of location sensors on surgical instruments relative to the locations of anatomical structures shown on the tomographic image in order to determine the position of the surgical instrument in the nasal cavity. In embodiments, one of a number of different registration strategies may be used including intrinsic strategies and as extrinsic strategies.

For example, in embodiments, registration is performed as an intrinsic registration strategy known as anatomical fiducial registration. With anatomical fiducial registration, a number of fiducial markers are placed at specific anatomical locations on the patient's body during the preoperative tomographic scan and during the surgical procedure. These fiducial markers are typically positioned on the patient's head or face at locations that correspond to specific anatomical landmarks within the ears, nose and/or throat. The fiducial markers may be mounted on a head set or frame that is worn by the patient or the fiducial markers may be affixed directly to the patient's body (e.g., by adhesive attachment to the skin, anchoring into bone, etc.). In embodiments other registration strategies may be used to register the image of the nasal cavity to position of the patient's nasal cavity in a reference frame.

Once a registration process is completed, the ablation procedure may be performed. In embodiments, to correlate head position with the tracking system, the fiducial markers remain in fixed position on or in the patient's body until after the ablation procedure has been completed. Unlike some procedures, for example neurosurgical procedures, that require the patients head to be fixed in a rigid stereotactic frame, in embodiments that use fiducial markers mounted on or in the patient's body may allow for free movement and repositioning of the patient's head during the procedure, and the registration process may be continually performed so that the actual position of the patient's nasal cavity is correlated in the reference frame with the image of the nasal cavity.

The computer work station of the surgical navigation device is configured to display one or more image(s) on a monitor showing the image of the nasal cavity along with an indication, such as a cross hairs or a representation of the surgical instrument, of the real time position of the surgical instrument within the nasal cavity. The image of the nasal cavity may be displayed as any combination of two-dimensional plane views (e.g. sagittal plane, coronal plane, transverse plane), and three dimensional views. In this manner, a physician is able to view the precise position of each sensor-equipped instrument relative to the surrounding anatomical structures shown on the tomographic scan.

In embodiments the surgical navigation may include electromagnetic sensors/tracking systems where radiofrequency electromagnetic location sensors (e.g., electromagnetic coils) are placed on the surgical device and on a localizer frame worn by the patient. A transmitter is positioned near the operative field. The transmitter transmits signals that are received by the surgical instrument-mounted sensors and localize mounted sensors. The tracking system detects variations in the electromagnetic field caused by the movement of the instrument-mounted sensors relative to the transmitter, Examples of electromagnetic surgical navigation systems that may be used with the present technology include the Fusion ENT Navigation system available from Medtronic Navigation, Louiville, CO, Fiagon Navigation System from Fiagon GmbH Hennigsdorf, Germany, the KICK EM from Brainlab, Inc., Westchester, IL.

In embodiments, the surgical navigation system includes an electromechanical sensors/tracking systems that includes a multi jointed articulating mechanical arm attached to the surgical instrument. The multi-jointed articulating mechanical arm includes sensors to measure movements of the joints that are used to determine the location of the instrument based on signals received from the sensors.

In embodiments, the surgical navigation system includes optical sensors/tracking systems that detect/track optical navigation elements (e.g., infrared light emitting LEDs or passive markers) that are placed on the surgical instruments and detects/tracks a localizes frame worn by the patient. Camera(s) is/are positioned to receive light emitted or reflected from the navigation elements. Examples of optical tracking system that may be used with the technology herein is the LandmarX Evolution® ENT II Image Guidance System available from Medtronic Xomed Surgical Products, Inc., Jacksonville, Fla.; VectorVision® system and Kolibri® system available from BrainLAB, Inc., Westchester, IL.

The surgical navigation system may be used to track a surgical device, such as a surgical probe used for ablation of a tissue region within the nasal cavity. The surgical probe may have one or more location sensors that are trackable by the surgical navigation system. In embodiments, the location sensor may be built into the surgical device at the time of manufacture or may be attached immediately prior to or during use of the surgical device for the ablation procedure. In embodiments, one or more location sensors may be attached or integrated into any of the devices described in patent application publication number US 2015/0164571 A1, which is incorporated by reference herein.

Figure 2A:
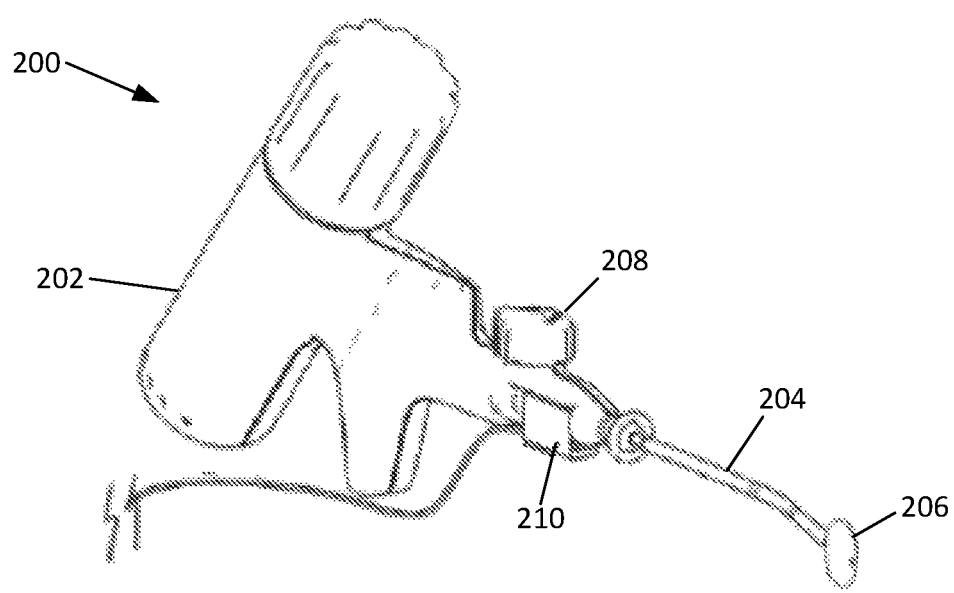
FIGS. 2A-2D show an embodiment of a surgical device with a removable location sensor.
Figure 2B:
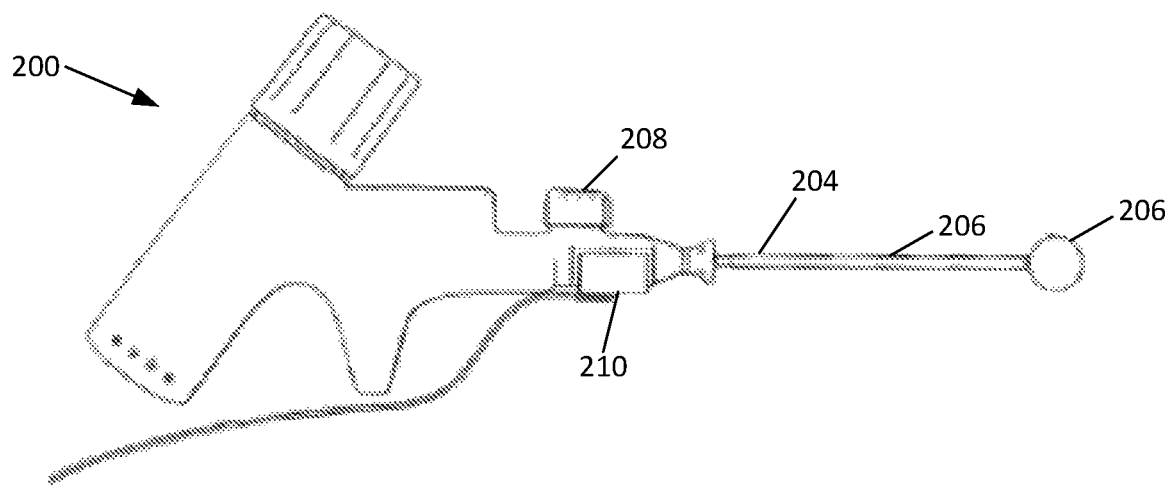

FIGS. 2A-2D show an embodiment of a surgical probe device 200. The surgical probe device includes a handle 202, an energy source (not shown) within the handle, a probe 204 shaft extending from the handle, an ablation end effector 206 in communication with the energy source, and an energy activation switch 208. In embodiments, for example as shown in FIG. 2A, a location sensor 210 is attached to a portion of the handle. As noted above, during an ablation procedure, location sensors or markers mounted on the surgical device communicate with or are detected by the surgical navigation system in order to indicate the position of each location sensor in order to determine the position and orientation of the surgical device, and in embodiments the position and orientation of the end effector. The surgical navigation system correlates the data or signal received from the location sensors with the reference frame of the image of the nasal cavity and the actual position of the nasal cavity.

Figure 3A:
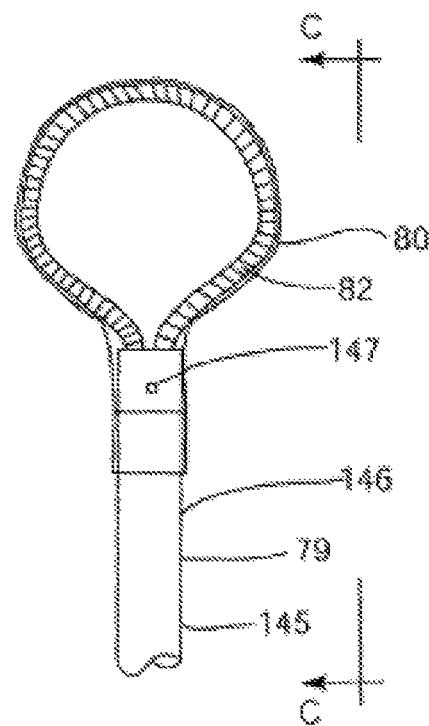
FIGS. 3A-3F show embodiments of an end effector.
Figure 3B:
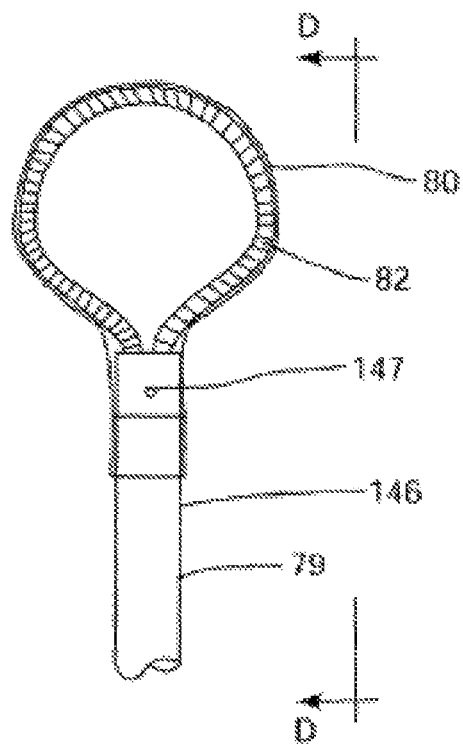
Figure 3C:
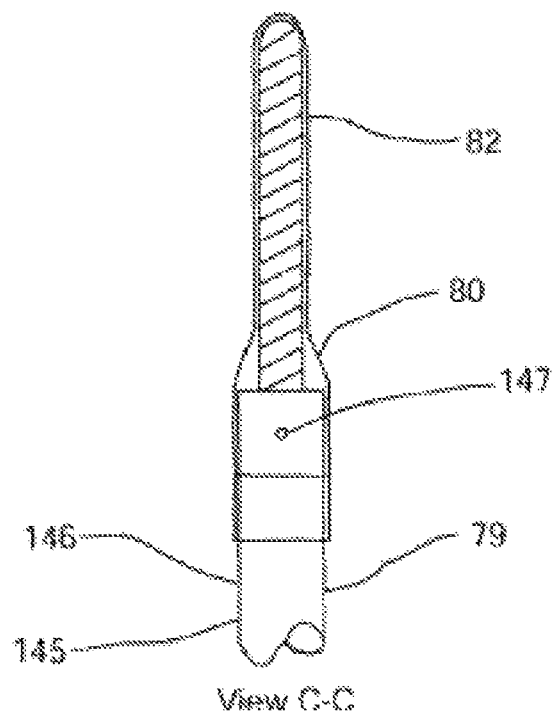
Figure 3D:
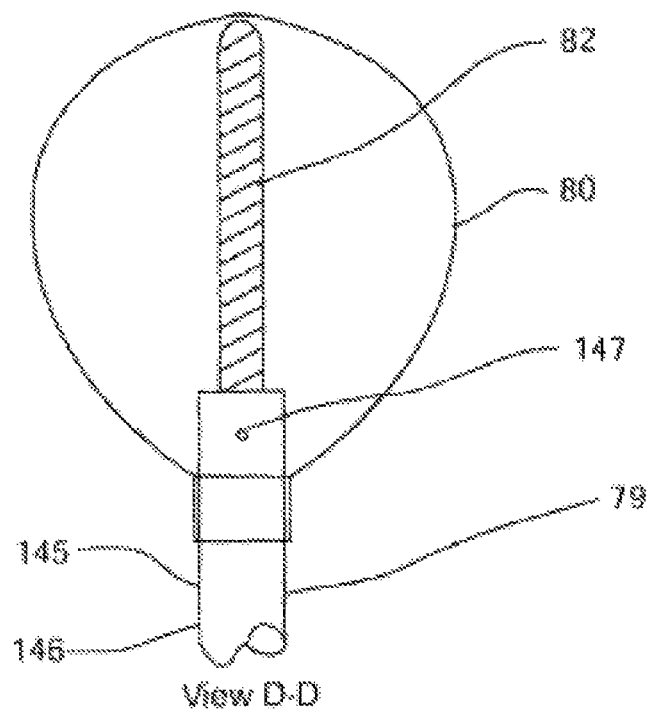

FIGS. 3A-F show embodiments of ablation end effectors that may be used with the technology disclosed herein. FIG. 3A is a schematic illustration of a side view of and embodiment of a distal end of a surgical probe 79 comprising expandable membranous structure 80 encompassing spring-like structure 82. Spring-like structure 82 is configured as a loop structure as depicted. Expandable membranous structure 80 is depicted in its un-expanded state. FIG. 3B is a schematic illustration of the same side view in FIG. 3A of surgical probe 79 with its expandable membranous structure 80 in its expandable state, FIG. 3C is a schematic side view illustration taken at view C-C from FIG. 63. FIG. 63 is a schematic side view illustration taken at view D-D from FIG. 3B. Surgical probe 79 is configured with expandable membranous structure 80 functioning as a liquid cryogen evaporation chamber. Liquid cryogen enters the interior of expandable membranous structure 80 from encompassed spring-like structure 82. Evaporated cryogen gas exits the interior of expandable membranous structure 69 through fenestration(s) in distal end 146 of probe shaft 145 and exits surgical probe 79 proximally into the room. Spring-like structure 82 is configured to pre-tension expandable membranous structure 80 in one radial axis to a greater extent than a second radial axis in a manner that causes expansion to be constrained in the radial axis with greatest pre-tensioning. In FIGS. 3A and 3B, spring-like structure 82 is configured to pre-tension membranous structure 80 to a greater extent in the radial axis that is normal to the view axis. In FIGS. 3C and 3D, spring-like structure 82 is configured to pre-tension expandable membranous structure 80 to a greater extent in the radial axis that is parallel to the view axis. FIG. 3A and FIG. 3C depict surgical probe 79 with expandable membranous structure 80 in its un-expanded state. FIGS. 3B and 3D depict surgical probe 79 with expandable membranous structure 80 in its expanded state. Pre-tensioning of expandable membranous structure 80 provides a means for achieving a predetermined expanded shape for optimal matching of the morphology of the target area of the lateral nasal wall.

Figure 3E:
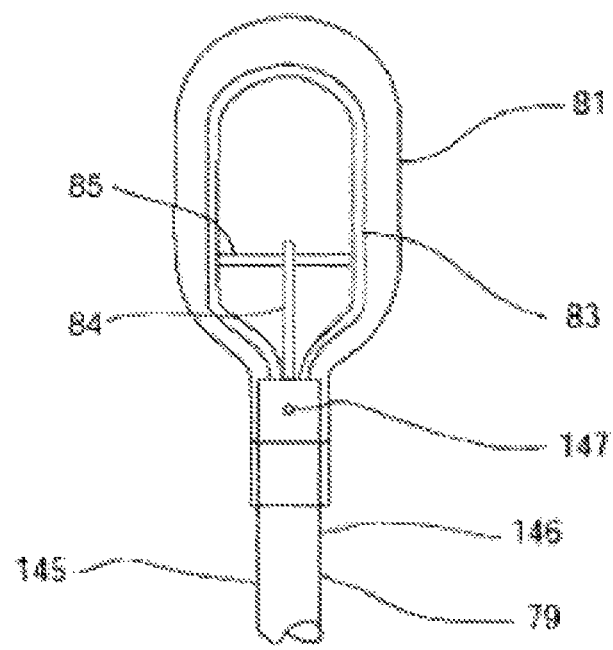
Figure 3F:
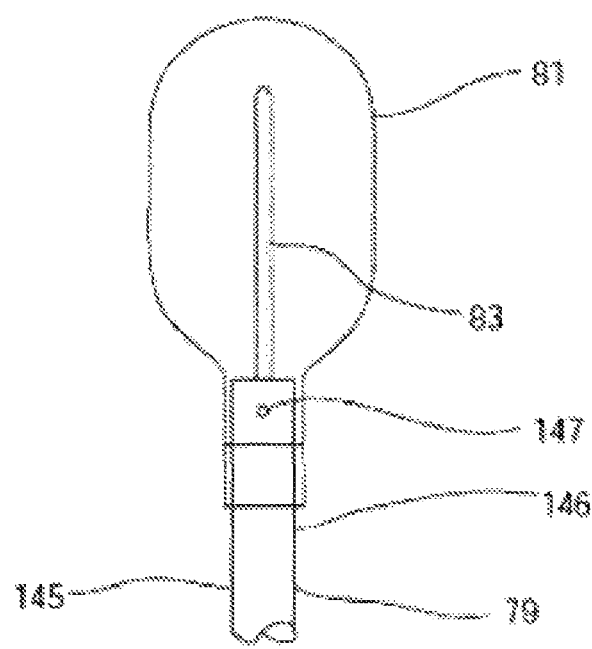

FIG. 3E shows a side view of an embodiment including a structure or member 83 which is formed into a looped and elongated structure having arcuate edges for presenting an atraumatic surface. Rather than being formed as a spring like structure, the structure 83 may be formed of a relatively rigid wire or member instead which maintains its configuration when pressed against a tissue surface. Structure 83 may form a continuous structure which defines an opening there through such as a looped or elongated and looped member which is open through the loop. The structure 83 may be contained entirely within the expandable structure 81 which may be formed to have a predefined shape which is distensible or non-distensible when inflated by the cryogen. Moreover, the expandable structure 81 may be formed to surround the structure 83 entirely without being supported by or attached to the structure 83 itself. Such a structure 83 may provide a configuration which presents a low-profile as the device is advanced into and through the nasal cavity and between the nasal turbinate tissues. Yet because of the relatively flattened shape and rigidity and integrity of the structure 83, the structure 83 may be used to manipulate, move, or otherwise part the tissues of the nasal cavity without having to rely upon the expandable structure 81. Additionally, the low-profile enables the structure 83 to be positioned desirably within the narrowed confines of, e.g., the cul-de-sac in proximity to the posterior nasal nerves. When the expandable structure 81 is in its deflated state, it may form a flattened shape and when inflated, the expandable structure 81 may inflate into a configuration which remains unsupported by or attached to the structure 83. Because the structure 83 may be formed of a member which solid along its length, the cryogen may be introduced directly into the expandable structure 81 through a distal opening defined in the probe shaft 145.

Figure 2C:
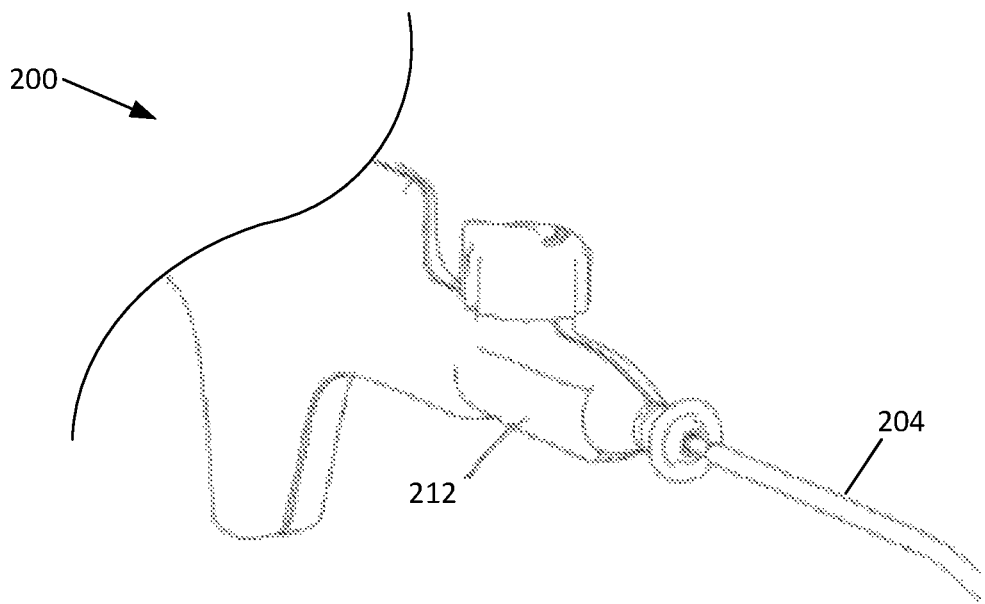
Figure 2D:
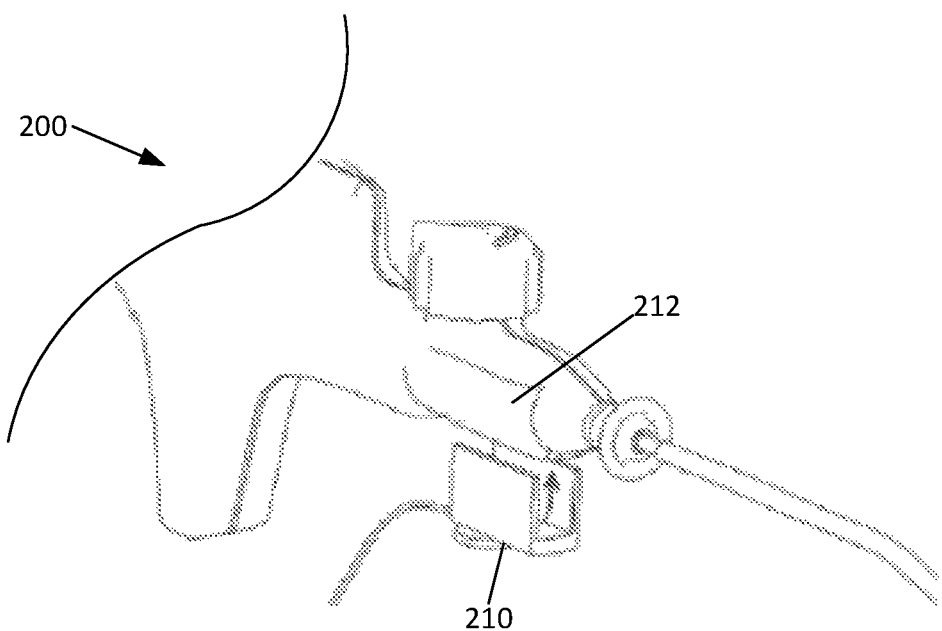

In embodiments, for example as shown in FIGS. 2A-2D, surgical device 200 may include surfaces configured to receive a removable location sensor. For example, as shown in FIGS. 2C and 2D, handle portion includes a detent 212 comprising flat opposing parallel walls that are configured to receive location sensor 210. The detent 212 is configured to prevent movement of the location sensor 210 relative to the surgical device 200 so that the relative locations of other portions of the surgical device relative to the location sensor remain constant during the procedure. As shown, in this configuration the location sensor 210 is positioned on the most distal end of the handle 202 which is a portion of the device that remains outside of the nasal cavity during an ablation procedure. This location has the advantage of ensuring the location sensor remains in the navigation field; i.e. reference frame, throughout the procedure without obstructing direct visualization or additional tool paths. As will discussed in greater detail below, after a removable location sensor is attached to a surgical device, the assembly may be calibrated so that the relative location of the distal end effector is known relative to the location sensor. Once the instrument is calibrated with the sensor, the physician can track the end effector inside the nasal cavity with the surgical navigation system. In embodiments, location sensors can be attached to the proximal end of the cannula in a similar manner as a Fiagon adapter.

Figure 4A:
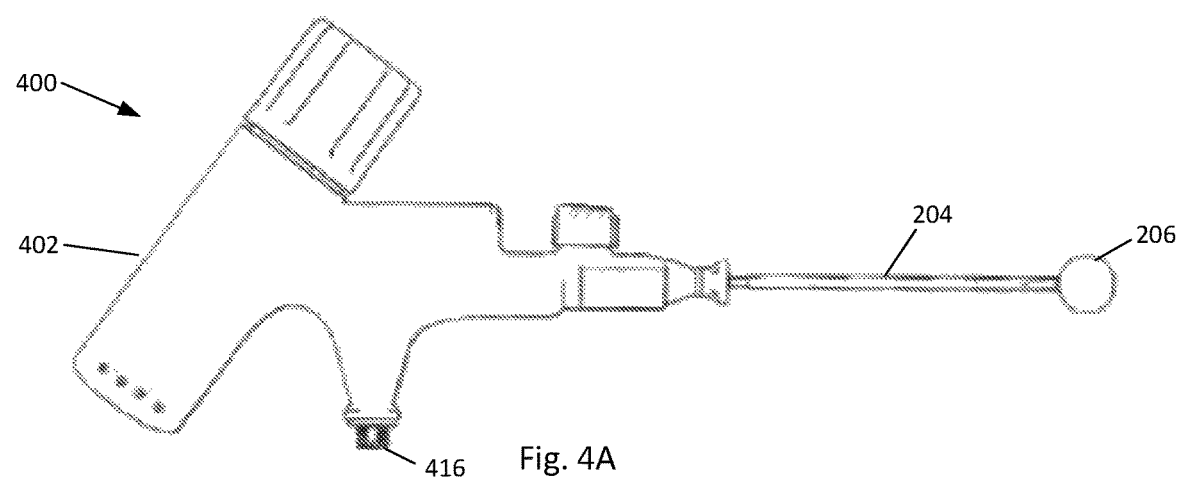
FIGS. 4A-4G show embodiments of a surgical device with imbedded location sensors.
Figure 4B:
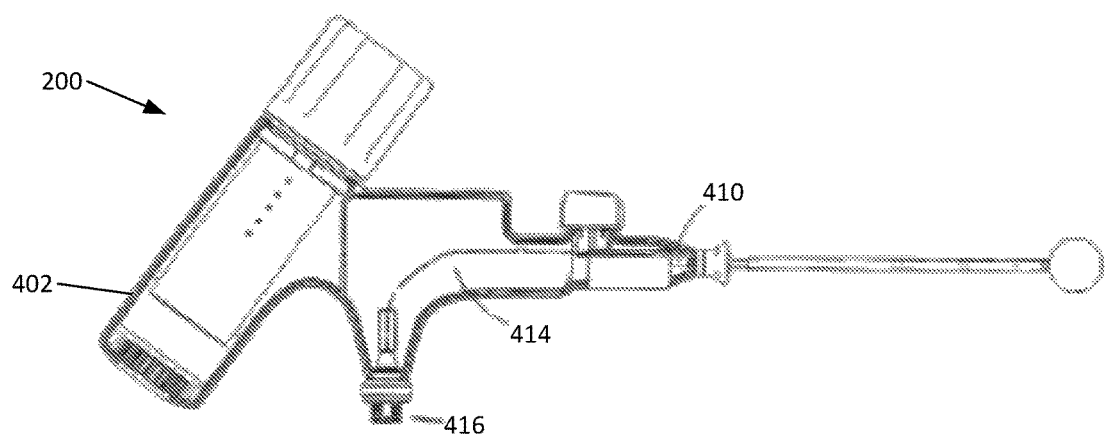
Figure 4C:
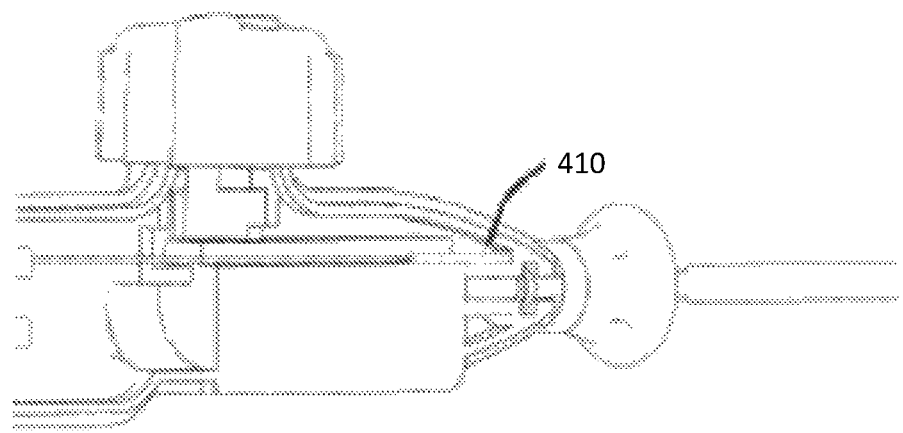
Figure 4D:
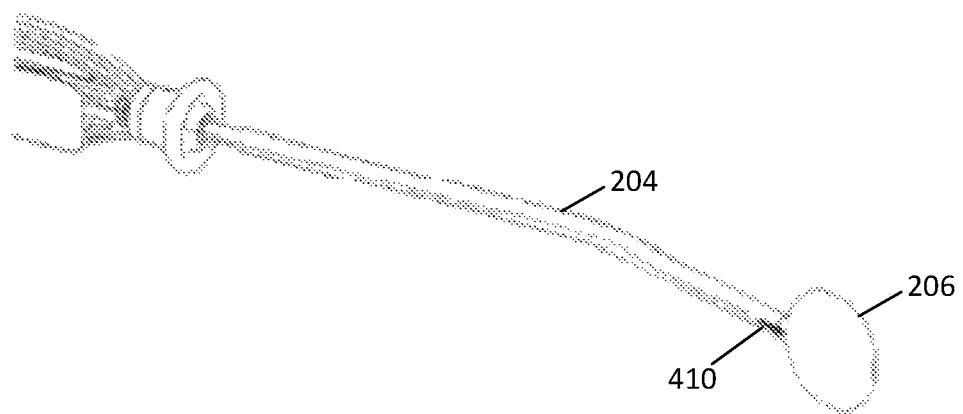

In embodiments, for example as shown in FIGS. 4A-4G, location sensors 410 may be integrated internally in the surgical device 400. For example, a location sensor 410 may be imbedded into the handle 402 as shown in FIGS. 4A-4C. In embodiments where the location sensor 410 is wired the wiring 414 may extend out of a port 416 in the handle of the surgical device. The handle may include a bracket to fix the location sensor and further the location sensor may be attached using standard attachment methods (e.g. epoxy, adhesive). In embodiments with imbedded location sensors, the location sensors may be pre-calibrated to the distal tip and/or ablation end effector at the time of manufacture or prior to a procedure being performed. Pre-calibration may eliminated the need to calibrate the position of the location sensor relative to the ablation end effector at the time of the procedure. In embodiments, the location sensor 410 may be positioned at any location on the surgical device, for example proximate to where the ablation end effector attaches to the probe shaft, as shown in FIG. 4I/Location sensors located on or proximate to the end effector have the advantage of allowing the position of the end effector to be determined more precisely particularly in embodiments where the probe shaft or end effector are malleable or semi-rigid and do not maintain their relative position in relation to the handle portion of the surgical device. In embodiments, the location sensors may be the Aurora 5 DOF or Aurora Mini 6 DOF from NDI, Ontario, Canada.

Figure 4E:
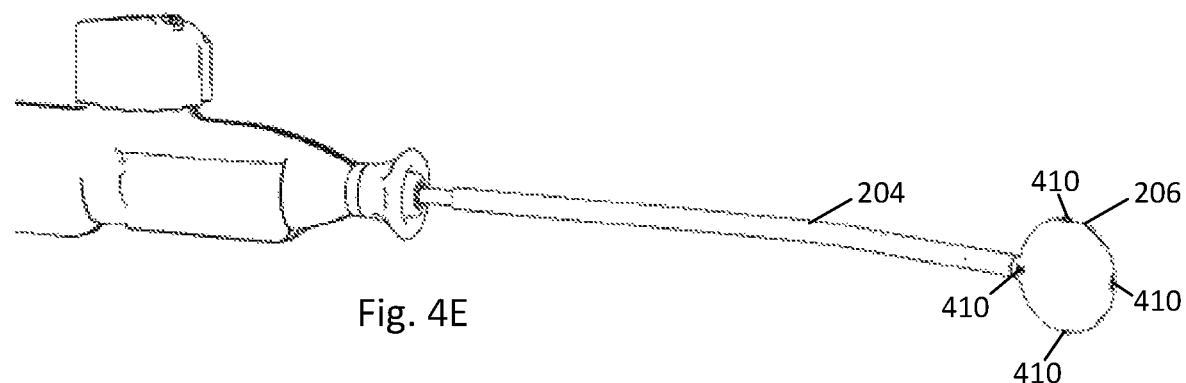
Figure 4F:
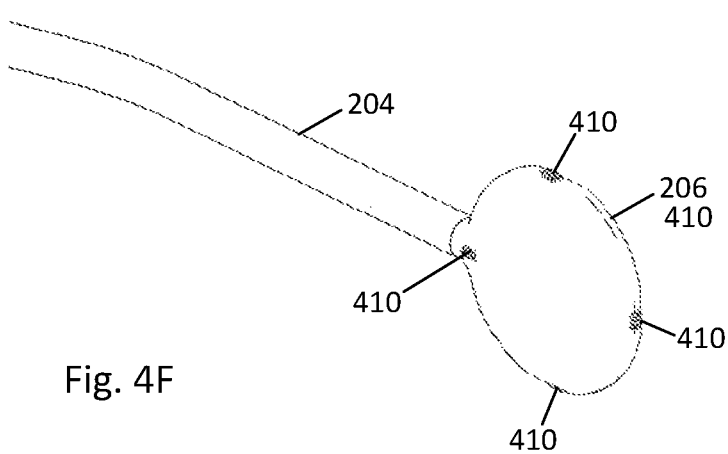
Figure 4G:
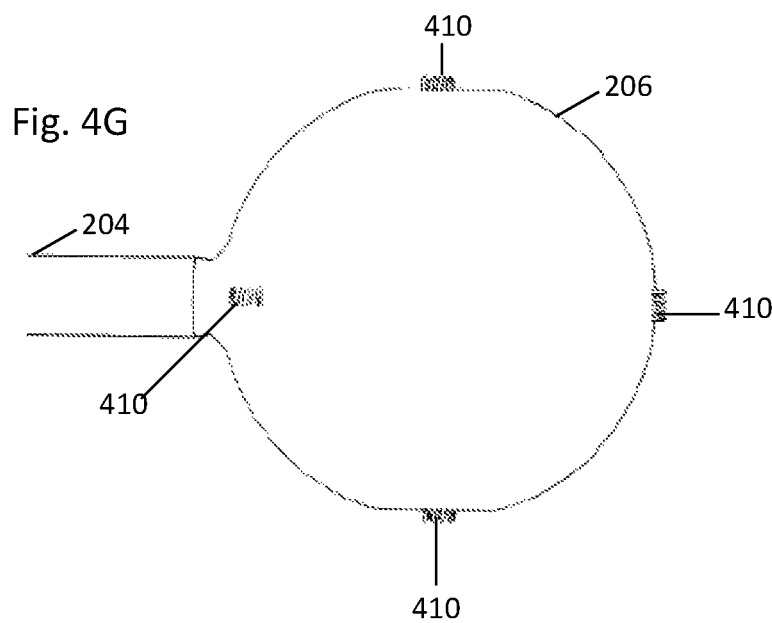
Figure 5A:
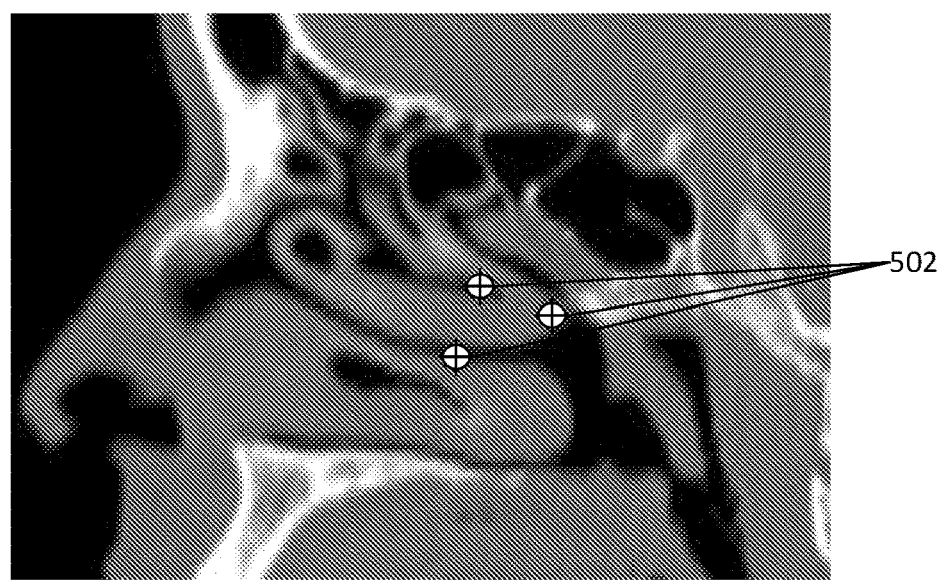
FIGS. 5A-5C show an embodiment of an alignment process.
Figure 5B:
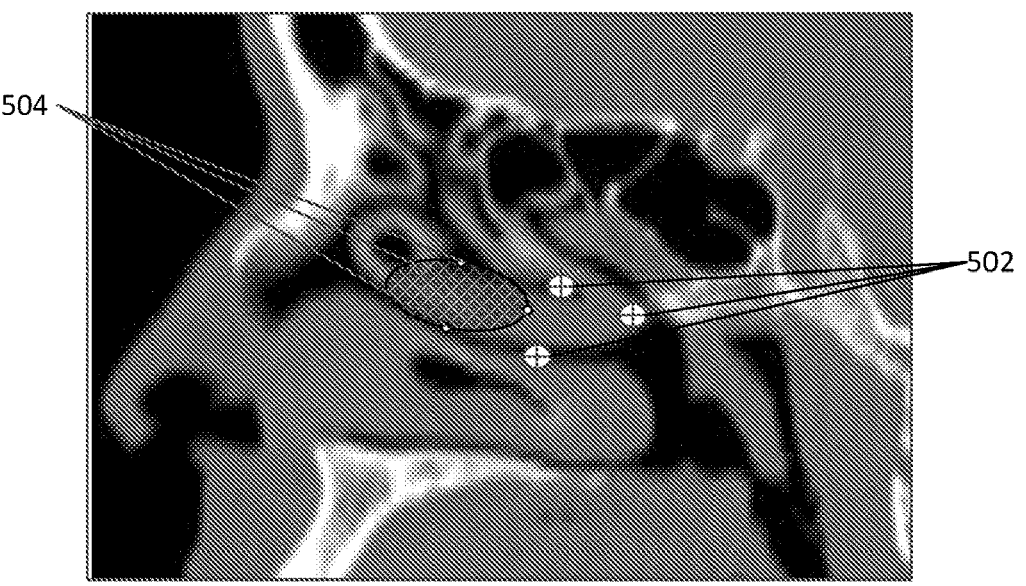
Figure 5C:
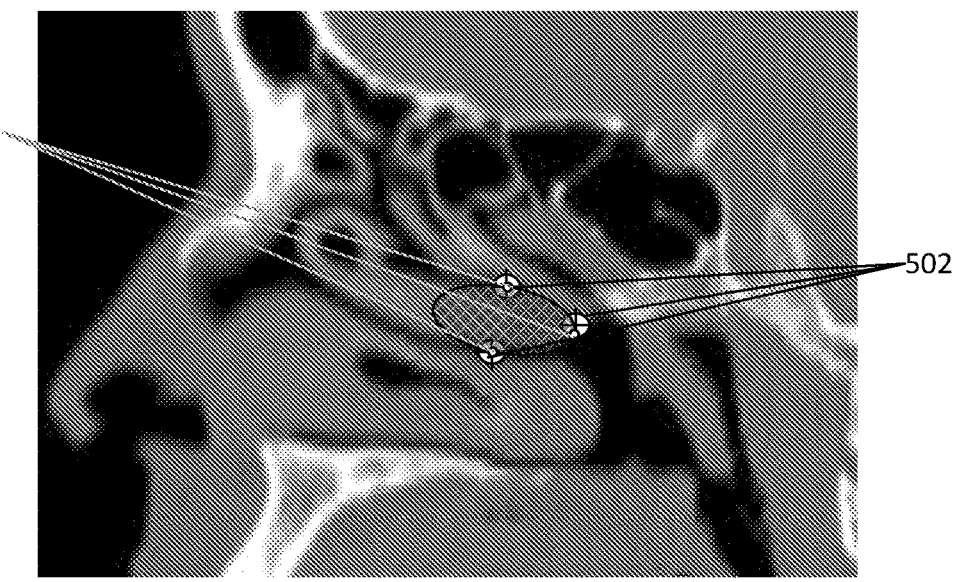

In embodiments, for example as shown in FIGS. 4E-4G, location sensors 410 may be placed on or within an ablation end effector 206 in a plane configuration, for example in a circular pattern. The ablation end effector may include a planar member that the location sensors are disposed on. In embodiments the plurality of sensors may be in other configurations, for example a line, circle, square, or another unique geometry that provides an area in a 2-D plane for treatment. The location of the location sensors of the plane may be displayed by the surgical navigation system and used to position and orient the surface of the end effector onto a target treatment surface of a patient's mucosal surface. As shown in FIG. 5A prior to performing an ablation procedure, reference points 502 with the same relative geometry to each other as the location sensors may be established in the reference frame of the image of the nasal cavity. During the procedure representations 504 of the location sensors displayed by the surgical navigation system, as shown in FIG. 5B, may be navigated within the nasal cavity to align within a range of the reference points 502, as shown in FIG. 5C, in order to position the surface of the ablation end effector at the desired target treatment location. Navigation using a plurality of location sensors and reference points provides the advantage of achieving a precise location and orientation of the end effector.

Figure 6A:
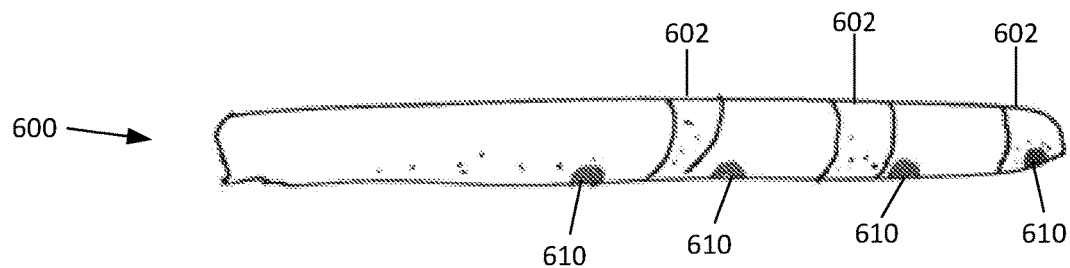
FIGS. 6A-6D show an embodiment of a radio ablation catheter with imbedded location sensors.
Figure 6B:
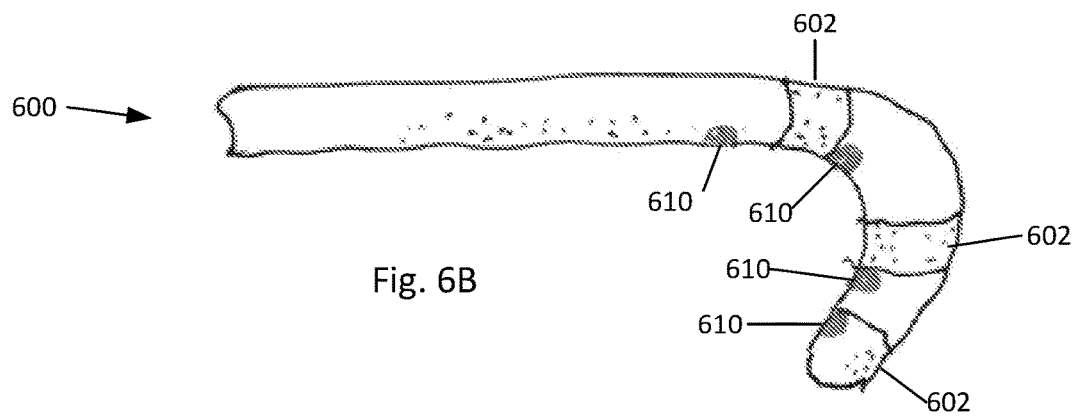
Figure 6C:
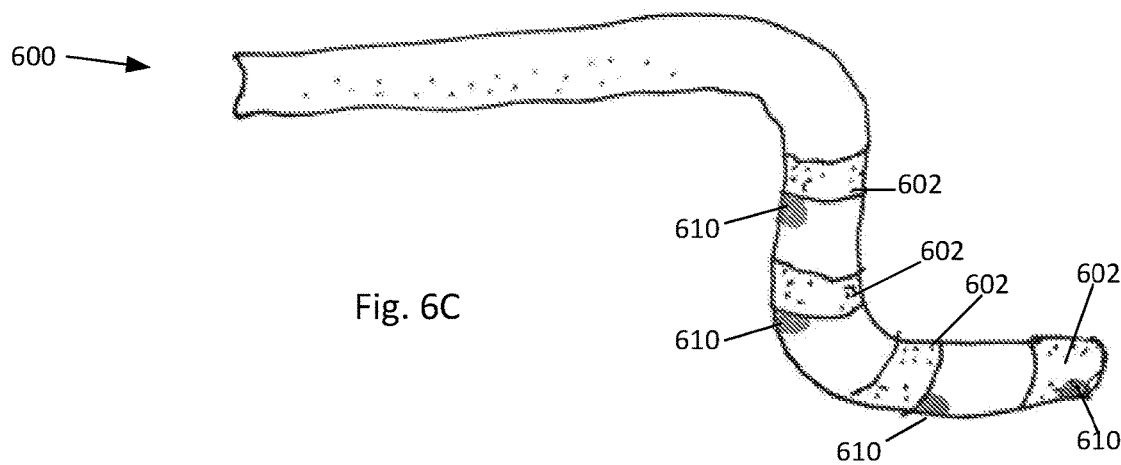
Figure 6D:
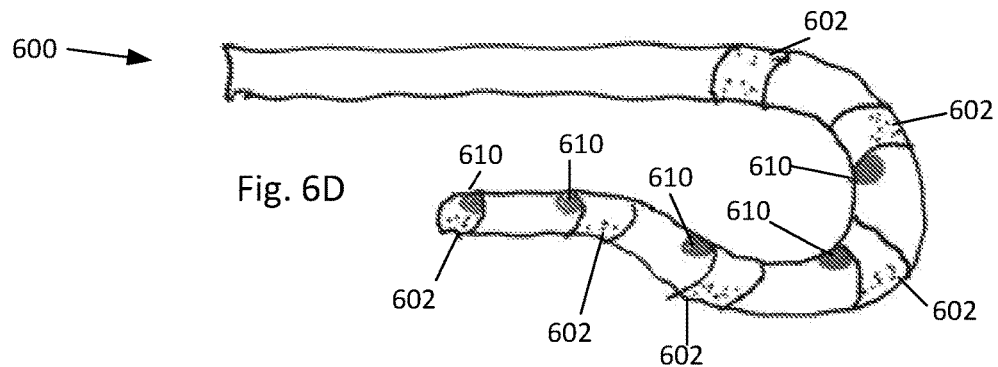

As discussed above, the end effector may be a cryoablation end effector, however, the target treatment position identification and navigation technology disclosed herein may also be used with other types of ablation. For example, as shown in FIGS. 6A-6D, in embodiments a surgical device may include a radiofrequency catheter 600 with a plurality of electrodes 602 disposed near a distal end. The electrodes 602 are configured to emit radio frequency energy which penetrate and ablate tissue. The catheter 600 can be articulated to form a semicircular structure, as shown in FIG. 6B, or a serpentine structure, as shown in FIGS. 6C and 6D. In embodiments, the catheter 600 may include location sensors 610, as discussed above, proximate to each electrode 602. The location sensors are detected by the surgical navigation system and the configuration, location, and orientation of the articulated distal end can be displayed in the reference frame over the image of the nasal cavity during an ablation procedure.

Figure 7:
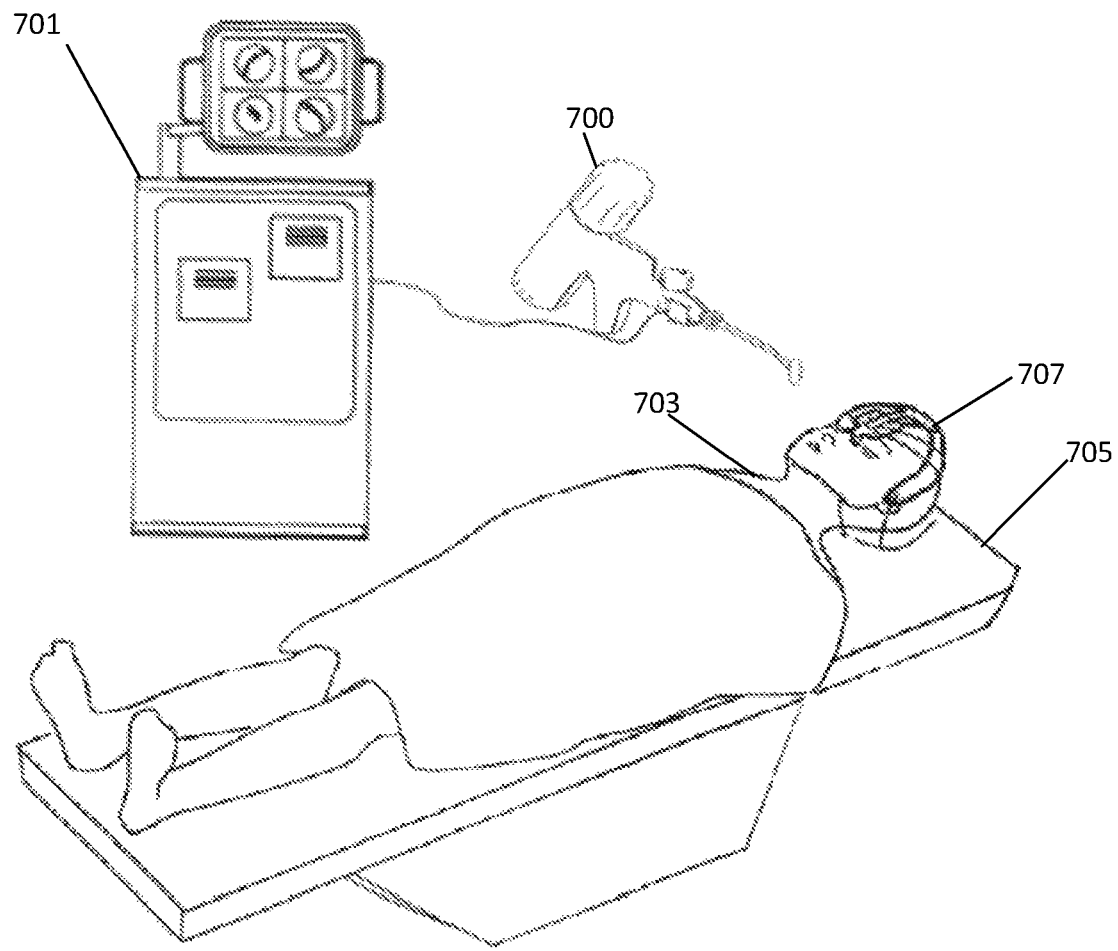
FIG. 7 shows an embodiment of a system including a surgical navigation system and a surgical device.
Figure 8:
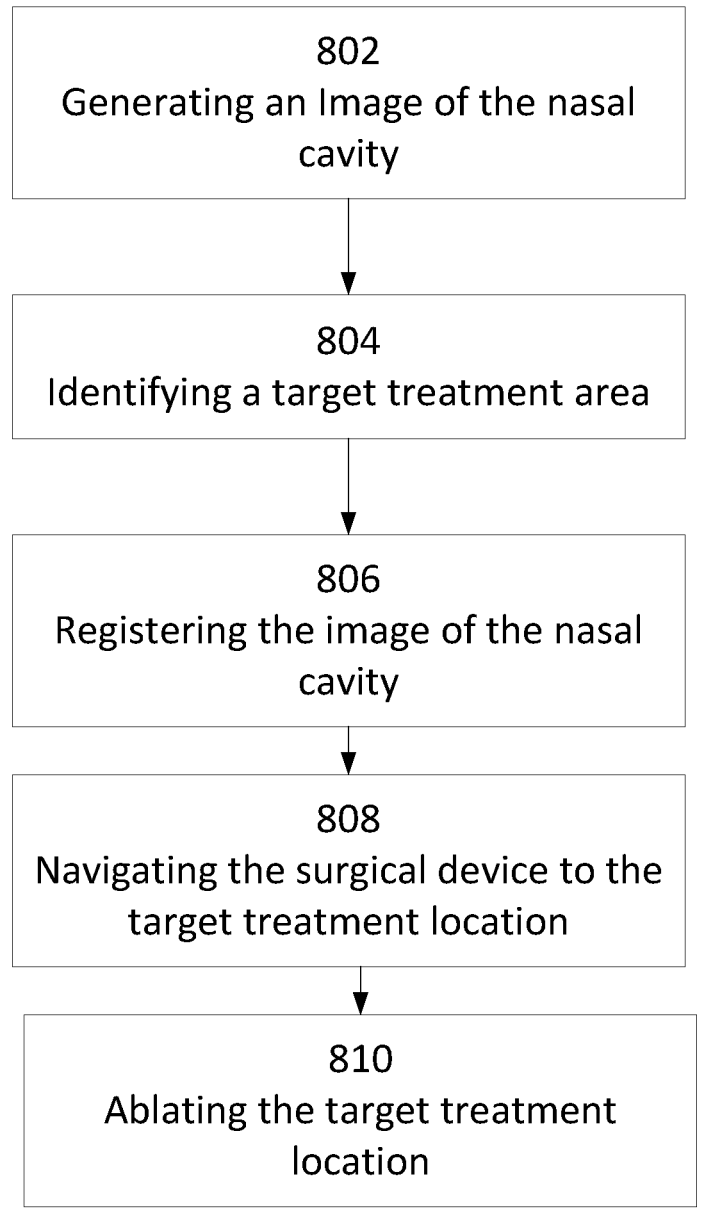
FIG. 8 shows a flowchart of an embodiment of a method for performing an ablation procedure.

In embodiments, a system, as shown for example in FIG. 7, including a surgical navigation system 701 and a surgical device 700, as discussed above, may be used during the performance of identifying and treating a nerve within the nasal cavity of a patient. As shown in FIG. 8, an embodiment of a method includes generating an image of the nasal cavity 802, identifying a target treatment location 804, registering the image of the nasal cavity with the position of the nasal cavity and the surgical device 806, navigating the surgical device to the target treatment location using the surgical navigation system 808, and performing ablation at the target treatment location 808.

A discussed above, an image of the nasal cavity may be generated from a preoperative scan of the patient's nasal cavity. The image of the nasal cavity may be analyzed by a physician and/or image recognition software to determine a target treatment location in order to ablate a desired nerve. The target treatment location may be determined by identifying anatomical landmarks in the image of the nasal cavity and using predetermined relations of nerves locations relative to the anatomical landmarks. In embodiments, the anatomical landmarks are not identifiable visually with an imaging device within the nasal cavity. For example, the landmarks are covered by mucosa and can only be identified through scans (e.g. CT, X-ray, or MRI scans) that enable seeing under the mucosa surface without physically cutting and removing the surface.

The anatomical landmark may be one or more of the sphenopalatine foramen, the ethmoid crest; the inferior turbinate bony ridge, the intersection of a posterior fontanelle and a perpendicular plate of a palatine bone, the anterior nasal spine, the most posterior attachment point of the middle turbinate to the lateral wall; and the piriform aperture. The landmarks may be used to determine the location of innervation and the nerve trajectory in order to determine a target treatment location to ablate the nerve at the determined location.

In embodiments, the target treatment location may be determined based on one or more of size of the landmark, location of the landmark, distance and direction to another other landmark, and stored relations between anatomical structures and nerves. The determined target treatment location may be visually displayed to a physician overlaid on the image of the nasal cavity in order to assist the physician in positioning a surgical device at the target treatment location during the ablation procedure.

In embodiments, the target treatment location may be defined by a plurality of reference points. As noted above, the relative geometry of the reference points may correspond to the relative geometry of a plurality of location sensors on an end effector of a surgical device. For example, three reference points may be defined including a first reference point corresponding to an intersection of a posterior fontanelle and a perpendicular plate of a palatine bone; a second reference point corresponding to the sphenopalatine foramen; and a third reference point corresponding to a ridge of an inferior turbinate.

The target treatment position may be stored as a visual overly on the image of the nasal cavity. The visual overlay may include an indication of the location of the target treatment area. For example the target treatment area may be a point in the image of the nasal cavity or stored as a surface having a different color than the surrounding surface in the image of the nasal cavity. In embodiments, the target treatment location may be determined during the ablation procedure without pre-identifying the target treatment position.

In embodiments, the location sensors of the surgical device are calibrated to the position of the end effector prior to performing the ablation procedure in order to ensure that the surgical navigation system show a precise location of the surgical device in the reference frame of the image of the nasal cavity. In embodiments, a calibration tool for use in calibrating the surgical navigation system to a surgical device including location sensors. In embodiments calibration is performed on surgical devices that has a substantially fixed shape wherein the location sensor is not attached proximate the end effector. The calibration tool may comprise a substantially rigid body having a receiving groove, and a first calibration tip. The calibration tool may further include a second calibration tip. In embodiments, the first and second calibration tips extend in 180 degree opposite directions from one another. The surgical device is insertable into the receiving groove with its distal end positioned in a known position relative to the first and second calibration tips. The first and second calibration tips are alternately placeable in a known location relative to an electromagnetic transmitter such that readings may be taken by the surgical navigation system and used to calibrate the surgical navigation system to the distal portion, particularly the end effector of that medical device. Once calibrated, the end effector is registered in the reference frame and may be displayed with the image of the nasal cavity to show the real time position of the end effector. As noted above, in embodiments, the location sensors of the surgical device may be pre-calibrated.

With the location sensors of the surgical device registered, the surgical device may be used to perform an ablation procedure at the target treatment location. To perform the ablation procedure, the patient 703 may be positioned on an operating table 705, as shown in FIG. 7, and the nasal cavity may be registered with the pre-operative image of the nasal cavity. For example, as discussed above, registration may be done with a localizer frame 707 with fiducial markers attached to the head. However, as discussed above, other registration strategies may be used based on the type of location sensors used by the surgical navigation system.

The surgical navigation system is configured to display a one or more superimposed images of an indication of the position of the surgical device over the image of the nasal cavity on a display. The physician may use the displayed indication of the surgical device to place the end effector into the nasal cavity and be positioned at the target treatment location. As noted above, the surgical navigation system may display an indication of the target treatment location over the image of the nasal cavity. In embodiments an imaging device, e.g. an endoscope, within the nasal cavity may be used to assist in navigating the surgical device. The surgical navigation system may display an image from the imaging device adjacent to the images of the nasal cavity. Displaying the image of the nasal cavity has the advantages of allowing a physician to overcome the shortcomings of endoscopic imaging including being spatially limited, being two dimensional, and only having a line-of-sight view. In embodiment a combination of landmarks visible with the imaging device and landmarks visible in the image of the nasal cavity but not the imaging device may be used to determine the target treatment location.

The physician navigates the surgical device using the indication of the end effector on the display of the surgical navigation system to align the end effector with the target treatment location. In embodiments including multiple location sensors in a plane, as shown in FIGS. 4E-4G, and a plurality of reference points defining the target treatment location, the physician may navigate the surgical device using the display of the surgical navigation system to align each location sensor to align with a reference point in order to place a surface of the end effector against a target treatment surface.

Once the end effector is desirably placed against the target treatment position, the therapy may be applied. Such therapy may include heat, such as thermoablation, or cold, such as cryotherapy (cryoablation), radio ablation or chemical ablation. In embodiments, the ablation is cryoablation and cryogen liquid is delivered through a small delivery tube as described in commonly owned U.S. patent application Ser. No. 14/503,060 filed Sep. 30, 2014, entitled "APPARATUS AND METHODS FOR TREATING RHINITIS", which as previously noted is incorporated herein by reference in its entirety for all purposes.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby

The invention claimed is:

1. A system for treating a tissue region within a nasal cavity, comprising:
   a surgical navigation device; and
   a surgical probe comprising an ablation end effector and one or more location sensors that are detectable by the surgical navigation device,
   wherein the surgical navigation device is configured to:
      indicate a target treatment location of the tissue region on an image of the nasal cavity, and
      register the image of the nasal cavity to the nasal cavity to establish a reference frame,
   wherein the ablation end effector is configured to be insertable into the nasal cavity and positioned at the target treatment location using a location of the one or more location sensors in the reference frame,
   wherein the ablation end effector is configured to ablate the target treatment location when the ablation end effector is determined to be at the target treatment location, and
   wherein at least one location sensor of the one or more location sensors is coupled to a handle of the surgical probe.

2. The system of claim 1, wherein the target treatment location is a surface in the nasal cavity and the surface is defined by (i) a first reference point corresponding to an intersection of a posterior fontanelle and a perpendicular plate of a palatine bone, (ii) a second reference point corresponding to a sphenopalatine foramen, and (iii) a third reference point corresponding to a ridge of an inferior turbinate,
   wherein the ablation end effector comprises a planar member,
   wherein the one or more location sensors comprise three location sensors on the planar member, and
   wherein the surgical navigation device is configured to determine that the ablation end effector is located at the target treatment location by determining that each of the three location sensors are aligned with a respective one of the first reference point, the second reference point, and the third reference point.

3. The system of claim 2, wherein the surgical navigation device comprises a display configured to provide an indication of the location of each of the three location sensors relative to the first reference point, the second reference point, and the third reference point of the target treatment location.

4. The system of claim 1, wherein the target treatment location is a surface in the nasal cavity and the surface is defined by (i) a first reference point corresponding to an intersection of a posterior fontanelle and a perpendicular plate of a palatine bone, (ii) a second reference point corresponding to a sphenopalatine foramen, and (iii) a third reference point corresponding to a ridge of an inferior turbinate,
   wherein the one or more location sensors comprise three location sensors located on or within an expandable structure of the ablation end effector coupled to a distal end of the surgical probe, and
   wherein the ablation end effector is configured to ablate the target treatment location by introducing a cryogenic fluid into the expandable structure such that the expandable structure inflates from a deflated configuration into an expanded configuration against the surface of the target treatment location.

5. The system of claim 4, wherein the surgical navigation device comprises a display configured to provide an indication of the location of each of the three location sensors relative to the first reference point, the second reference point, and the third reference point of the target treatment location.

6. The system of claim 1, wherein the image of the nasal cavity is based on a computed tomography scan.

7. The system of claim 1, wherein the image of the nasal cavity is based on a magnetic resonance imaging scan.

8. The system of claim 1, wherein the ablation end effector is configured to ablate the target treatment location by at least one thermal therapy selected from a group of thermal therapies consisting of: cryotherapy, cryoneuromodulation, cryomodulation, cryolysis, cryoablation, and thermoablation.

9. The system of claim 1, wherein the surgical navigation device comprises a sensor tracking system that is configured to track the location of the one or more location sensors based on at least one signal selected from among a group of signals consisting of: an optical signal and an electromagnetic signal.

10. The system of claim 1, wherein the handle comprises a detent that is configured to removably couple with the at least one location sensor.

11. The system of claim 1, wherein the at least one location sensor is coupled a distal end of the handle that is configured to remain outside of the nasal cavity when the ablation end effector ablates the target treatment location.

12. The system of claim 1, wherein the at least one location sensor is located at an internal portion of the handle.

13. The system of claim 1, wherein the ablation end effector comprises a plurality of electrodes that are configured to a radiofrequency energy to ablate the target treatment location.

14. The system of claim 13, wherein, for each electrode, a respective location sensor of the one or more location sensors is located proximate to the electrode.

15. The system of claim 1, wherein the surgical navigation device is configured to determine the target treatment location using image recognition software.

16. A system for treating a tissue region within a nasal cavity, comprising:
   a surgical navigation device; and
   a surgical probe comprising an ablation end effector and one or more location sensors that are detectable by the surgical navigation device,
   wherein the surgical navigation device is configured to:
      indicate a target treatment location of the tissue region on an image of the nasal cavity, and
      register the image of the nasal cavity to the nasal cavity to establish a reference frame,
   wherein the ablation end effector is configured to be insertable into the nasal cavity and positioned at the target treatment location using a location of the one or more location sensors in the reference frame,
   wherein the ablation end effector is configured to ablate the target treatment location when the ablation end effector is determined to be at the target treatment location, and
   wherein indicating the target treatment location comprises identifying a sphenopalatine foramen in the image of the nasal cavity.

17. The system of claim 16, wherein surgical navigation device is configured to determine the target treatment location by measuring a predetermined distance from the sphenopalatine foramen in the reference frame.

18. The system of claim 17, wherein surgical navigation device is configured to determine the target treatment location by measuring a predetermined direction from the sphenopalatine foramen in the reference frame.

19. A system for treating a tissue region within a nasal cavity, comprising:
   a surgical navigation device; and
   a surgical probe comprising an ablation end effector and one or more location sensors that are detectable by the surgical navigation device,
   wherein the surgical navigation device is configured to:
      indicate a target treatment location of the tissue region on an image of the nasal cavity, and
      register the image of the nasal cavity to the nasal cavity to establish a reference frame,
   wherein the ablation end effector is configured to be insertable into the nasal cavity and positioned at the target treatment location using a location of the one or more location sensors in the reference frame,
   wherein the ablation end effector is configured to ablate the target treatment location when the ablation end effector is determined to be at the target treatment location,
   wherein the surgical navigation device further comprises a localizer frame that is configured to be worn by a patient, and
   wherein the localizer frame comprises at least a portion of the one or more location sensors.

20. The system of claim 19, wherein the ablation end effector is configured to ablate the target treatment location by at least one thermal therapy selected from a group of thermal therapies consisting of: cryotherapy, cryoneuromodulation, cryomodulation, cryolysis, cryoablation, and thermoablation.

* * * * *